(12) United States Patent
Qian

(10) Patent No.: US 9,175,321 B2
(45) Date of Patent: Nov. 3, 2015

(54) R-PRAZIQUANTEL PREPARATION METHOD

(71) Applicant: SUZHOU TONGLI BIOMEDICAL CO., LTD, Jiangsu (CN)

(72) Inventor: Mingxin Qian, Jiangsu (CN)

(73) Assignee: SUZHOU TONGLI BIOMEDICAL CO., LTD, Jiangsu (CN)

( * ) Notice: Subject to any disclaimer, the term of this patent is extended or adjusted under 35 U.S.C. 154(b) by 0 days.

(21) Appl. No.: 14/353,485

(22) PCT Filed: Oct. 26, 2012

(86) PCT No.: PCT/CN2012/083611
§ 371 (c)(1),
(2) Date: Apr. 22, 2014

(87) PCT Pub. No.: WO2013/060292
PCT Pub. Date: May 2, 2013

(65) Prior Publication Data
US 2014/0256003 A1    Sep. 11, 2014

(30) Foreign Application Priority Data

Oct. 26, 2011    (CN) .......................... 2011 1 0327992

(51) Int. Cl.
C12P 17/12    (2006.01)
C12P 17/18    (2006.01)
C07D 471/04    (2006.01)
C12P 41/00    (2006.01)
C07D 217/12    (2006.01)

(52) U.S. Cl.
CPC .............. *C12P 17/182* (2013.01); *C07D 217/12* (2013.01); *C07D 471/04* (2013.01); *C12P 17/12* (2013.01); *C12P 41/00* (2013.01)

(58) Field of Classification Search
None
See application file for complete search history.

(56) References Cited

FOREIGN PATENT DOCUMENTS

| CN | 1608052 A | 4/2005 |
|---|---|---|
| CN | 101445507 A | 6/2009 |
| CN | 102093346 A | 6/2011 |
| JP | 1228964 A | 12/1989 |

OTHER PUBLICATIONS

Paal, A.T., et al., "Lipase-catalyzed kinetic resosultion of 1,2,3,4-tretahydroisoquinoline-1-aetic acid esters", Yrytsfrfton:Asymmetry 19 (2008) 2784-2788.
Roszkowski, P., et al., "Enantioselective synthesis of (R)-(−)praziquantel (PZQ)", Tetraheron: Asymmetry 17 (2006) 1415-1419.

*Primary Examiner* — Nashaat Nashed
(74) *Attorney, Agent, or Firm* — K&L Gates LLP; Louis C. Cullman; Michelle Glasky Bergman

(57) ABSTRACT

Provided are R-praziquantel preparation methods, which utilize the characteristics of biological enzyme of strong stereoselectivity, site-selectivity, and regioselectivity, of high resolution efficiency, of mild reaction conditions, and of simple operations to catalyze the hydrolysis of a certain enantiomer in a chemically synthesized racemate or a derivative, thus acquiring a mixture of reacted and unreacted optical isomers. R-praziquantel prepared by the method can have a purity of 98% or more.

10 Claims, No Drawings

R-PRAZIQUANTEL PREPARATION METHOD

FIELD OF INVENTION

The present invention relates to the field of pharmaceutical preparation, in particular, to a method of preparing R-praziquantel and the intermediate thereof.

BACKGROUND OF INVENTION

Praziquantel, also referred to as Biltricide, is a broad-spectrum anti-parasitic medicament. It has a broad helminthic spectrum, and works on killing *Schistosoma japonica, Schistosoma haematobia, Schistosoma mansoni* and the like. Moreover, it also works on killing *Paragonimus (Paragonimus westermani), Clonorchis endemicus, hydatid, cysticercus, Sparganum mansoni, Fasciolopsis buski,* cestode, etc. Praziquantel is provided with characteristics of high efficacy, short treatment period, low dosage, fast metabolism, low toxicity and convenience for oral administration. The discovery of praziquantel brought a significant breakthrough in the parasistic chemotherapy, which has now become the drug of choice for treating various helminthiasis.

Praziquantel was first synthesized by Seubert, et al. in 1975, and two German pharmaceutical companies, E-Merck and Bayer successfully developed this medicament. It was first brought to market by E-Merck, Inc., with a trade name of Cesol in 1980, and has now been widely used in the world. Besides human use, it is also used for anti-parasitic treatment in animals, fowls, etc. However, toxic and harmful compounds (substances or reagents), such as potassium cyanide, cyclohexanoyl sulphoxide chloride and so forth, are required during the conventional preparation of praziquantel which also requires a long process route and harsh experimental conditions.

Recently, optical isomers of R-praziquantel and S-praziquantel were obtained through resolution of racemic praziquantel by Chinese researchers and discoveries were made from preclinical and early clinical trials that R-praziquantel is the active component of praziquantel against worms, and S-praziquantel is an inactive and even deleterious component; R-praziquantel provides better clinical efficacy than praziquantel at the same dose. Although the World Health Organization has been expecting to develop R-praziquantel to replace praziquantel, the technical problem of low yield in the chemical synthesis of R-praziquantel has been a pending issue for years, see the synthesis scheme above.

SUMMARY OF THE INVENTION

To solve the problems existing in the prior art aforementioned, the present invention provides a method for preparing R-praziquantel and R-nitroacid intermediate thereof, wherein the use of virulent potassium cyanide and sodium cyanide is avoided, largely elevating the safeness of the process and being conductive to environment.

The technical solutions of the invention are as follows. According to the first aspect of the invention, provided herein is a method for preparing an intermediate of R-praziquantel, wherein the chemical formula of this intermediate is illustrated as formula (4) and the method comprises the step of hydrolyzing compound of formula (2) by lipase at a temperature of 0-80° C., to give compound of formula (4), a R-nitroacid intermediate of R-praziquantel;

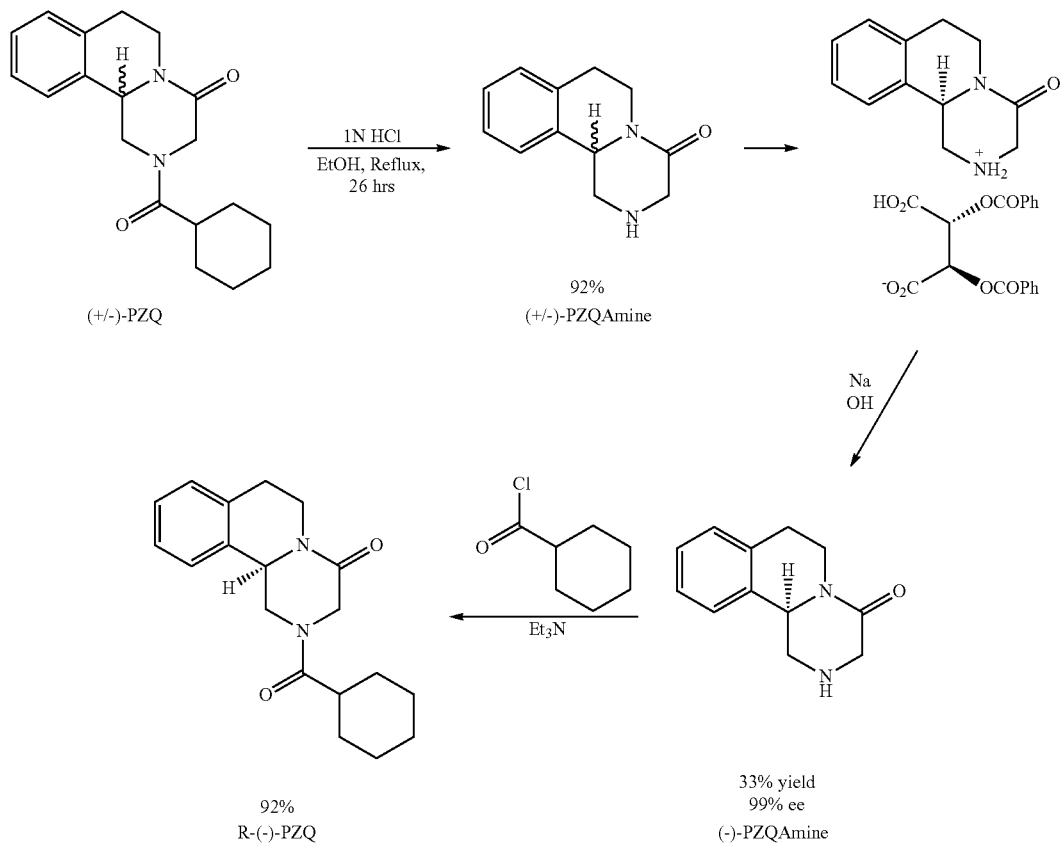

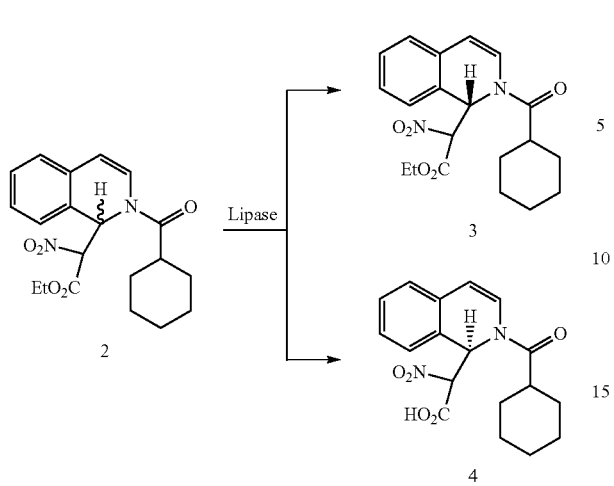

This method is based on lipase stereoselective ester-hydrolysis, wherein racemic nitroester (the compound of formula (2)) is hydrolyzed by lipase to give the R-nitroacid intermediate (the compound of formula (4)), and thus the S-nitroester intermediate (the compound of formula (3)) is separated therefrom through resolution.

The compound of formula (2) is commercially available or can be prepared manually. The present invention provides a method for preparing the compound of formula (2), wherein the method comprises the step of allowing the compound of formula (1) to react with ethyl nitroacetate and cyclohexanoyl chloride in a solvent to give the compound of formula (2).

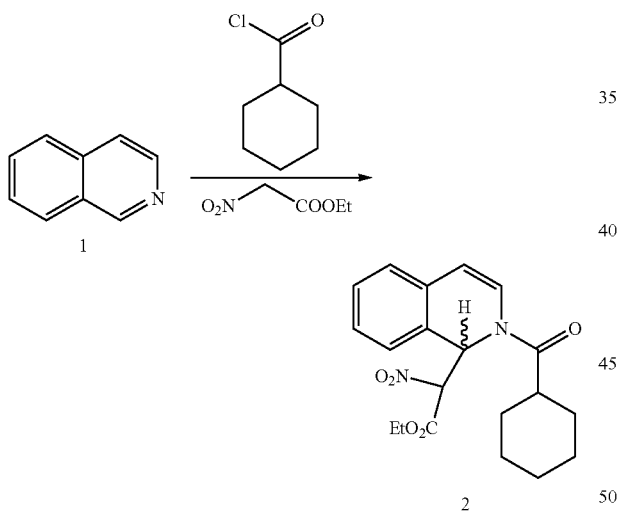

Preferably, the lipase includes, but not limited to, the lipase derived from *Aspergillus niger, Candida cylindracea, Rhizomucor miehei, Candida antarctica, Pseudomonas cepacia, Pseudomonas fluorescens, Thermomyces lanuginose, Bacillus subtilis, Fusarium solani pisi, Alcaligenes sp., Rhizopus niveus, Mucor javanicus, Rhizopus oryzae*, and *Fusarium solani pisi*.

Preferably, the lipase is *Thermomyces lanuginosus* lipase (SG165400, 100 u/mg), or *Candida antarctica* lipase (SG063906, 1 u/mg), or *Candida rugosa* lipase (SG061360, 2 u/mg), or *Pseudomonas cepacia* lipase (SG-061357, 30 u/mg), or *Pseudomonas fluorescens* lipase (SG075907, 40 u/mg), and the lipases described above can be purchased from Guangzhou Howei Chemical Co., LTD or other commercial sources. It should be emphasized particularly that only S-nitroester can react with the lipase used in the present invention to give S-nitroacid intermediate.

Preferably, the feed ratio by mass between the compound of formula (2) and the lipase in the hydrolysis described above is 100:0.5-100:3.

More preferably, the hydrolysis described above is carried out in a solvent containing phosphate butler solution.

Still more preferably, the hydrolysis described above is allowed to be carried out for 1-48 hours.

According to the second aspect of the invention, provided herein is a method for preparing R-praziquantel, comprising the following steps:

(a) preparing a compound of formula (4)-R-praziquantel intermediate according to the method previously described; (b) decarboxylating the compound of formula (4) in an organic solvent to give a compound of formula (5); (c) catalytically hydrogenating the compound of formula (5) in an organic solvent to give a compound of formula (6); and (d) allowing the compound of formula (6) to react with chloroacetyl chloride in an organic solvent to give a compound of formula (7), R-praziquantel;

wherein the steps (b) and (c) are carried out in one-pot procedure, and the compound (4) due to its instability is directly subjected to decarboxylation in the solution without separation to give the compound of formula (5).

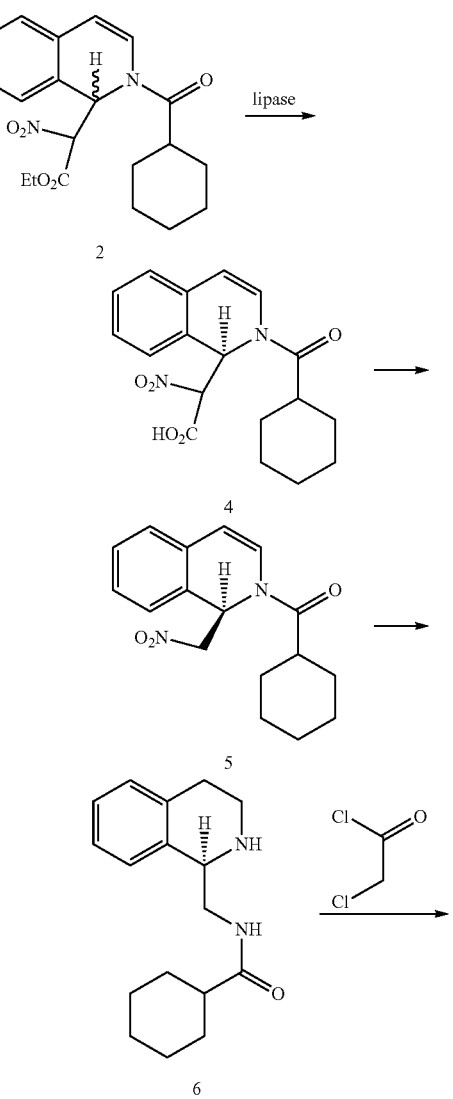

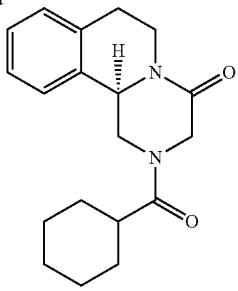

7

Wherein, as previously described, the preparation of the compound of formula (4) is based on lipase stereoselective ester-hydrolysis. in particular, racemic nitroester [a compound of formula (12)] can be hydrolysed by lipase to give R-nitroacid intermediate [the compound of formula (4)], and then S-nitroester intermediate [the compound of formula (3)] can he separated via resolution. R-nitro intermediate [the compound of formula (5)] is obtained through decarboxylation of the compound of formula (4), and is further catalytic hydrogenated to give an optically positive key intermediate R-amino [the compound of formula (6)]. The system used in the hydrogenation includes, but not limited to Ru/C, $H_2$/Pd-C systems, R-praziquantel can be obtained through the reaction between the compound of formula (6) and chloroacetyl chloride. The resolution of the racemic nitroesters in the method is achieved through forming S-nitroacid intermediate via lipase stereoselective ester-hydrolysis.

Also preferably, the lipase described above includes, but not limited to, the lipase derived from *Aspergillus niger, Candida cylindracea, Rhizomucor miehei, Candida antarctica, Pseudomonas cepacia, Pseudomonas fluorescens, Thermomyces lanuginose, Bacillus subtilis, Fusarium solani pisi, Alcaligenes sp., Rhizopus niveus, Mucor javanicus, Rhizopus oryzae*, and *Fusarium solani pisi*.

More preferably, the lipase is *Thermomyces lanuginosus* lipase (SG165400, 100 u/mg), or *Candida antarctica* lipase (SG063906, 1 u/mg), or *Candida rugosa* lipase (SG061360, 2 u/mg), or *Pseudomonas cepacia* lipase (SG061357, 30 u/mg), or *Pseudomonas fluorescens* lipase (SG075907, 40 u/mg), and the lipases described above can be purchased from Guangzhou Hopei Chemical Co., LTD or other commercial sources. It should be emphasized particularly that only S-nitroester can react with the lipase used in the present invention and give S-nitroacid intermediate.

Preferably, in step (c), the catalyst used in the catalytic hydrogenation is selected from the group consisting of 5% Ru containing Ru/C catalyst, 10% Pd containing Pd/C catalyst, and 10% Raney-Ni catalyst.

Further, in step (b), the organic solvent is one or more selected from the group consisting of DMSO, N-methyl-2-pyrrolidone, acetonitrile, and 1,4-dioxane.

Still further, in step (c), the organic solvent is one or more selected from the group consisting of absolute methanol, absolute ethanol, ethyl acetate, and tetrahydrofuran.

Again further, in step (d), the organic solvent is one or more selected from the group consisting of dichloromethane, methyl tert-butyl ether, and ethyl acetate.

According to the third aspect of the invention, provided herein is a method for preparing an intermediate of R-praziquantel, wherein the chemical formula of this intermediate is illustrated as formula (10), and the method comprises the following steps: (1) hydrolyzing the compound of formula (8) by nitrilase at a temperature of 0-80° C., to give a mixture of the compound of formula (9) and the compound of formula (10); and (2) separating the compound of formula (10) from the mixture obtained in step (2);

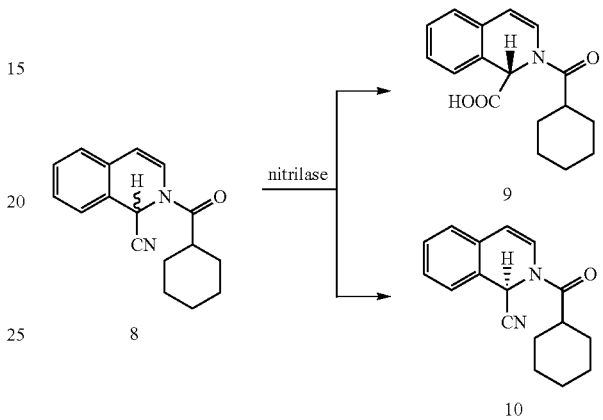

The nitrilase described above is selected from the group consisting of Arabidopsis-derived nitrilase, plant-derived nitrilase, fungi- and bacteria-derived nitrilase.

This method is based on the nitrilase stereoselective hydrolysis of the nitrite intermediate, the compound of formula (8). And the racemic nitrite intermediate, the compound of formula (8) is hydrolysed by nitrilase to give S-carboxylic acid intermediate, the compound of formula (9), such that the intermediate of R-praziquantel, the compound of formula (10) in R-configuration can be separated through resolution.

Wherein, the nitrilase used includes, but not limited to, nitrilases from *Arabidopsis*, nitrilases from plant (*Gramineae, Cruciferae, Musaceae*, etc.), nitrilases from fungi (*Fusarium, Aspergillus, Penicillium*, etc.) and bacteria (*Acinetobacter baumannii, Comamonas, Klebsiella, Pseudomonas, Nocardia, Rhodococcus*, etc.). It should be emphasized particularly that only nitrile intermediate in S-conformation can react with the nitrilase used in the invention and generate S-carboxylic acid intermediate, such that the intermediate of R-praziquantel, the compound of formula (10) in R-configuration can be separated.

Preferably, the nitrilase described above is derived from *Arabidopsis* (*Arabidopsis thaliana* NIT, Lonza Inc., Switzerland) or derived from *Aspergillus niger* (fungi) (*Aspergillus niger* K10, Leibniz-Institut DSMZ—Deutsche Sammlung von Mikroorganismen und Zellkulturen GmbH. (DSMZ)), or derived from *Alcaligenes faecalis* (bacteria) (American Type Culture Collection (ATCC)).

More preferably, the feed ratio by mass between the compound of formula 8) and the nitrilase in the hydrolysis described above is 100:0.5 100:3.

Still more preferably, the hydrolysis is allowed to be carried out for 1-48 hours.

Wherein, the compound of formula (8) is commercially available or can be prepared manually. The present invention provides a method for preparing the compound of formula (8), comprising the step of allowing isoquinoline (the compound of formula (1)) to react with potassium cyanide and cyclohexanoyl chloride to give the compound of formula (8).

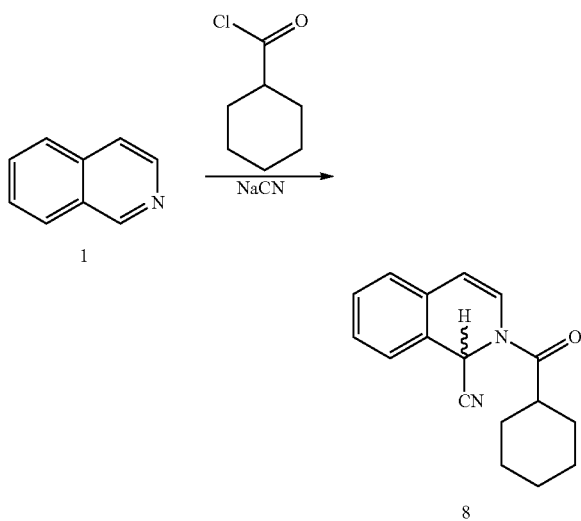

According to the fourth aspect of the invention, provided herein is a method for preparing R-praziquantel, comprising the following steps: (a') preparing the compound of formula (10) according to the method described above for the preparation of the compound of formula (10); (b') catalytically hydrogenating the compound of formula (10) obtained in step (a') in an organic solvent to give the compound of formula (6); and (c') annulating the compound of formula (6) obtained in step (b') with chloroacetyl chloride in an organic solvent to give R-praziquantel, the compound of formula (7).

that the intermediate of R-praziquantel, the compound of formula (10) in R-configuration can be separated through resolution. The hydrogenation of the R-nitrile intermediate gives optically positive key intermediate, R-amino-compound of formula (6), and $H_2$/Pd-C system and the like can be used in the hydrogenation. The final product, R-praziquantel, can be obtained from the reaction between the compound of formula (6) and chloroacetyl chloride. The resolution of the racemic nitrile intermediates can be achieved through formation of S-carboxylic acid intermediate via the nitrilase stereoselective hydrolysis, and then separation of the intermediate of R-praziquantel.

The nitrilase includes, but not limited to, nilrilases from *Arabidopsis*, nitrilases from plant (*Gramineae, Cruciferae, Musaceae*, etc.), nitrilases from fungi (*Fusarium, Aspergillus, Penicillium*, etc.) and bacteria (*Acinetobacter baumannii, Comamonas, Klebsiella, Alcaligenes faecalis, Pseudomonas, Nocardia, Rhodococcus*, etc.). It should be emphasized particularly that only nitrile intermediate in S-conformation can react with the nitrilase used in the invention and generate S-carboxylic acid intermediate.

Preferably, in step (b'), the catalyst used in the catalytic hydrogenation is selected from the group consisting of Ru/C catalyst, Pd/C catalyst, Pt/C catalyst, and Rh/C catalyst.

More preferably, in step (b'), the organic solvent is one or more selected from the group consisting of absolute methanol, absolute ethanol, isopropanol, acetic acid, and tetrahydrofuran.

Still more preferably, in step (c'), the organic solvent is one or more selected from the group consisting of dichloromethane, dichloroethane, ethyl acetate, and isopropyl acetate.

According to the fifth aspect of the invention, provided herein is a method for preparing intermediate (6) of R-praziquantel, wherein compound (11) is chosen as a raw material and allowed to react with compound (12) under the presence of lipase in an organic solvent, at a temperature of 0-75° C., followed by the separation of the mixture to obtain R-amino intermediate (6). Wherein, the lipase used is one or more selected from the group consisting of *Candida rugosa* lipase,

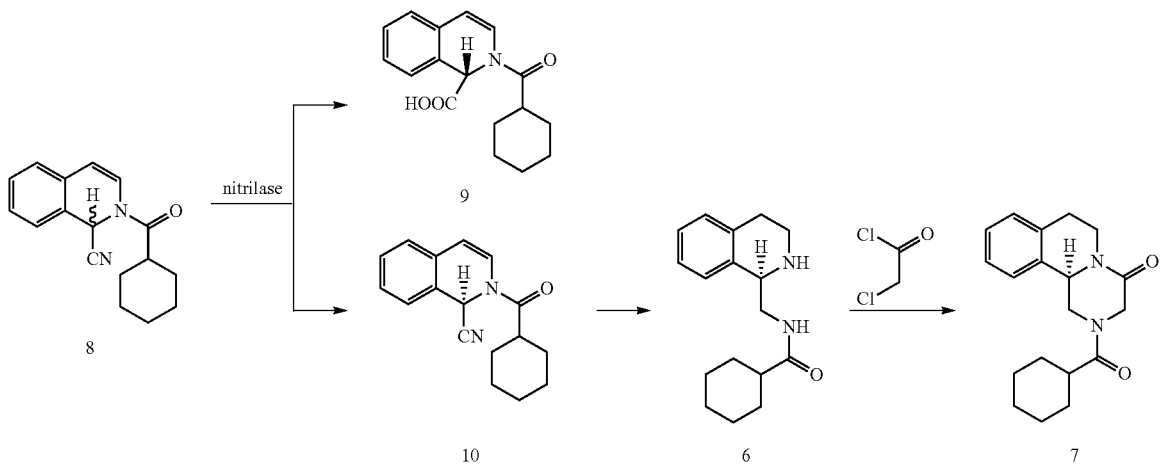

This method is base on the nitrilase stereoselective hydrolysis of the nitrite intermediate, the compound of formula (8). And the reaction of racemic nitrite intermediate, the compound of formula (8) under nitrilase generates the S-carboxylic acid intermediate, the compound of formula (9), such

*Candida antarctica* lipase-A (CAL-A) and *Candicia antarctica* lipase-B (CAL-B, Novozyme 435). The lipases described above are not limited to be from natural sources, but also include enzymes recombined through molecular biology procedures.

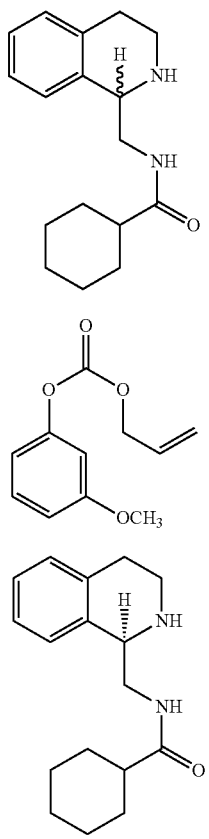

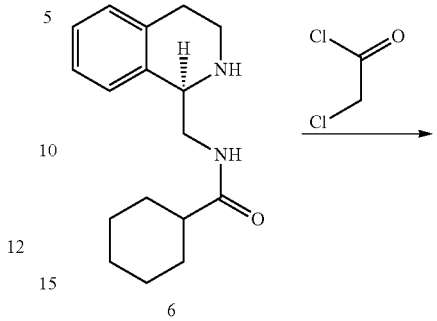

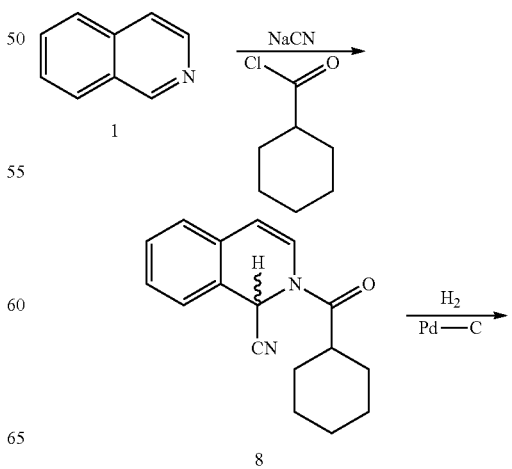

Secondary amine compounds (11) are stereoselectively acylated by lipase. Racemic secondary amine compound (11) is reacted with 3-methoxy-phenyl allyl carbonate compound (9) under lipase catalysis to give S-amide compound, before further separation to give optically positive key intermediate (6). The resolution of the racemic secondary amine is accomplished through the stereoselective acylation between the lipase and 3-methoxy-phenyl allyl carbonate compound (9). It should be emphasized particularly that only secondary amine in S-conformation can produce S-amide compound by reacting with the lipase used.

There is no restrictive requirement on the form of the lipase used, which can be in the forms of dry powder or immobilized enzyme, and immobilized enzyme is preferred, in particular, for the convenient post-processing and the advantage in recovering the enzyme.

Preferably, the organic solvent is one or more selected from the group consisting of toluene, tert-butyl methyl ether, ethyl ether, isopropyl ether, tetrahydrofuran, dichloromethane, hexane and acetonitrile.

Preferably, the reaction temperature can be controlled in a wide range and 0-75° C. is acceptable.

According to the sixth aspect of the invention, provided herein is another method for preparing R-praziquantel, comprising the following steps:

(1') preparing intermediate (6) according to the method for preparing intermediate of R-praziquantel described above; and (2') allowing the intermediate (6) prepared in step (1') to react with chloroacetyl chloride in an organic solvent under room temperature, after completion of reaction, adding benzyltriethylammonium chloride (catalyst), heating to reflux till the reaction is completed, separating and purifying the mixture to obtain R-praziquantel (7).

Preferably, the method for preparing R-praziquantel described above can further comprise the following steps:

(1") dissolving isoquinoline compound (1) and potassium cyanide in water within a reactor, adding cyclohexanoyl chloride to the reaction mixture dropwise with vigorously stirring and controlling the temperature of the reaction mixture no higher than −10° C.; after the addition, stirring the mixture for another 3-5 hours under 0° C.; separating and purifying at the end of the reaction to obtain racemic cyanogen intermediate (8); and (2") in a sealed container, adding the compound (8) prepared in step (1), a solvent and 10% catalyst Pd/C, and replacing the air in the sealed container with hydrogen before continuously feeding hydrogen to 3 MPa; heating the reaction mixture to 60-70° C., stirring for 4-5 hours, and at the end of the reaction separating and purifying the reaction mixture to obtain compound (11),

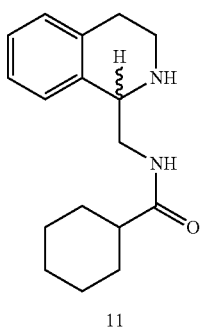

11

According to the seventh aspect of the invention, provided herein is a method for preparing intermediate of R-praziquantel, wherein the chemical formula of this intermediate is illustrated with formula (15), and the method is performed according to the following synthetic route:

positive compound (6), and the final product R-praziquantel (7) can be obtained through reaction between compound (6) and chloroacetyl chloride. The resolution of intermediate (15) and compound (14) is accomplished through stereoselective hydrolysis with protease. It should be particularly emphasized that only oxamate R-conformation can be reacted with the protease used to give R-oxalic acid.

There is no restrictive requirement on the form of the lipase used, which can be in the forms of dry powder or enzyme solution or immobilized enzyme, and immobilized enzyme is preferred, in particular, for the convenient post-processing and the advantage in recovering the enzyme.

Preferably, the pH value described above is 6.8 7.2.

More preferably, the reaction is stopped when the conversion reaches 40%-60%.

Preferably, the organic solvent is one or more selected from the group consisting of toluene, DMSO, ethanol, methanol, DMF, 1,4-dioxane, and acetonitrile.

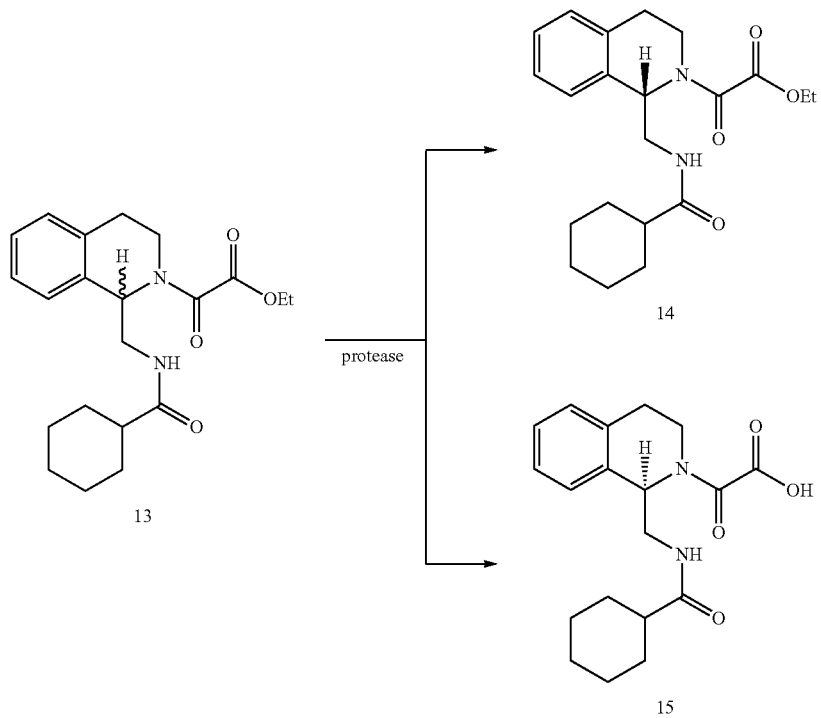

Compound (13) is chosen as a raw material in this method, and the reaction is carried out in an organic solvent under the presence of protease, at a temperature of 0-75° C., which is not stopped until the conversion reaches 38%-62%, after separation of the mixture, intermediate (15) is obtained. Wherein the protease used is one or more selected from the group consisting of papain, *Aspergillus* protease, *Bacillus* protease, *Bacillus licheniformis* protease, *Streptomyces griseus*, and chymotrypsin. The proteases described above are not limited to be from natural source, but also include enzymes recombined through molecular biology procedures:

This method is based on the protease stereoselective hydrolysis of a racemic oxamate compound: The racemic oxamate compound (13) can be separated via resolution into intermediate (15) and S-oxamate compound (14) by protease; intermediate (15) can be further reacted to form optically According to the eighth aspect of the invention, provided herein is a method for preparing R-praziquantel, comprising the following steps:

(1) preparing intermediate (15) according to the method described above for preparing intermediate (15);

(2) adding the intermediate (15) prepared in step (1) to HCl, heating to reflux till the reaction is completed, separating and purifying the mixture to obtain compound (6); and (3) allowing the compound (6) obtained in step (2) to react in an organic solvent with chloroacetyl chloride under room temperature, then adding benzyltriethylammonium chloride (catalyst) at the end of the reaction, heating to reflux till the reaction is completed, separating and purifying the mixture to obtain R-praziquantel (7),

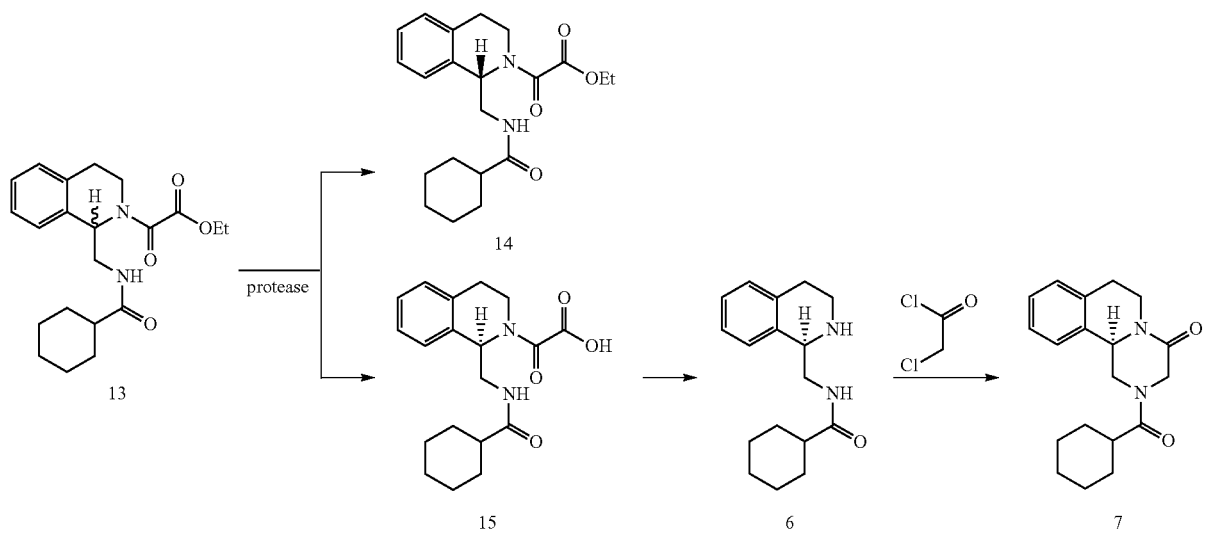

Preferably, the method described above for preparing R-praziquantel can further comprise the following steps:

(1) dissolving compound (1) and potassium cyanide in water within a reactor, adding cyclohexanoyl chloride dropwise to the reaction mixture with vigorously stirring and controlling the temperature of the reaction mixture no higher than −10° C.; after the addition, continuously stirring at 0° C. for 3-5 hours; after the reaction is finished, separating and purifying the mixture to obtain racemic cyanogen intermediate compound (8);

(2) adding compound (8) prepared in step (1), a solvent and 10% of catalyst Pd/C into a sealed container; replacing the air within the container with hydrogen before continuously feeding hydrogen to 3 MPa; heating the reaction mixture to 60-70° C. and stirring the reaction for 4-5 hours; after the reaction, separating and purifying the reaction mixture to obtain compound (11); and (3) adding compound (11) prepared in step (2), an organic solvent and sodium bicarbonate into a reactor, cooling the mixture to 8-12° C., adding the mixed solution of ethyl oxalyl monochloride and an organic solvent dropwise with stirring and controlling the temperature of the reaction mixture during this addition no higher than 15° C., after the addition, heating to room temperature and stirring the reaction for another 9-11 hours; separating and purifying the reaction mixture to obtain compound (13),

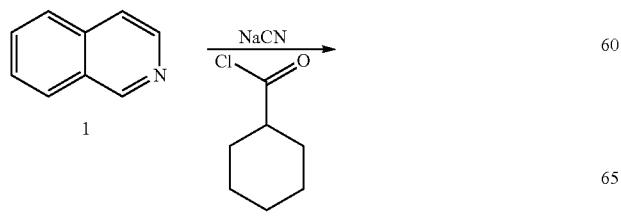

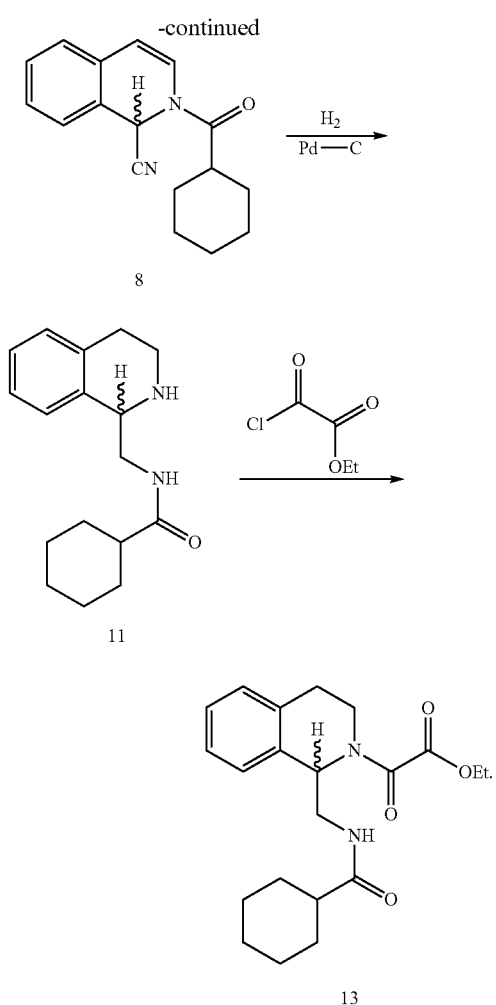

Employing the core technique in bio-enzyme catalysis, the present invention has developed a process for chiral synthesis of R-praziquantel with a high yield. Compared with the prior art, the invention, with a synthetic route through bio-enzyme catalysis, is provided with a number of advantages, and is more suitable and favorable for large-scale industrial production and environment protection. Based on the characteristics of bio-enzyme, such as highly specific stereoselectivity, site selectivity and regioselectivity, high resolution efficiency, mild reaction conditions, easy operation and so on, performing the synthesis from hydrolysis of the chemically synthesized raceme or a certain enantiomer in the derivates under catalyzing, the method can obtain a mixture of optical isomers reacted and unreacted, with a resolution mainly for preparing compounds such as chiral alcohols, acids, amines, esters, nitriles, amides and so on. These processes are technically mature, with easily available raw materials and low cost. The method of the invention can prepare R-praziquantel in a large-scale based on the simplified and optimized procedure, with a product purity higher than 98%, improving the quality standard, laying a foundation for developing and producing active pharmaceutical ingredients and formulations with high quality, and can therefore address the industrial difficulty in purifying praziquantel which has been a pending issue for almost 30 years, and pave the way for further preclinical and clinical druggability evaluation, the industrialization of R-praziquantel in large-scale, and thereby entering the international market.

DETAILED DESCRIPTION OF THE INVENTION

Further detailed description is made through particular examples below for the invention, which is however not limited to the following examples.

Example 1

In this example, a method is provided for preparing a R-nitroacid intermediate of R-praziquantel and R-praziquantel, specifically for following compounds.

I. Preparation of Compound of Formula (2)

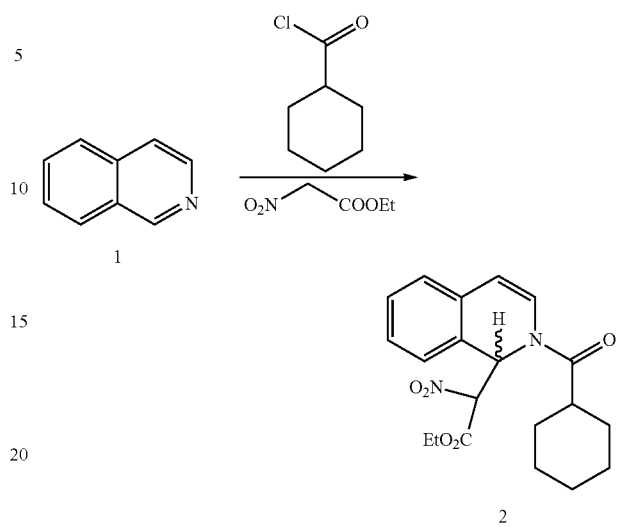

Into 300 mL acetonitrile, isoquinoline (42.62 g, 0.33 mol), lithium chloride (6.99 g, 0.165 mol, 0.5 eq) and ethyl nitroacetate (65.88 g, 0.495 mol, 1.5 eq) were added. With vigorously stirring, cyclohexanoyl chloride (53.21 g, 0.363 mol, 1.1 eq) was added dropwise to the mixed solution described above, with the temperature of the reaction mixture remained no higher than 25° C. After the addition, the stirring was continued under room temperature for 8-12 hours. HPLC indicated the reaction was complete, and the reaction mixture was concentrated under reduced pressure. The residue was purified by gel column chromatography (ethyl acetate:n-hexane=1:20) to obtain 105.6 g product as oil, i.e. compound of formula (2). Yield: 86%.

$^1$H NMR (CDCl$_3$, 400 MHz), δ (ppm): 1.28-1.31 (t, 3H, CH$_3$), 1.49-1.86 (m, 10H, 5xCH$_2$), 3.71-3.78 (1H, m, CH), 4.19-4.24 (m, 2H, —CH$_2$CH$_3$), 5.15 (d, 1H, CH), 5.37 (d, 1H, CH), 6.06 (d, 1H, CH), 6.60 (d, 1H, CH), 6.85-7.28 (m, 4H, ArH).

II. Preparation of Compound of Formula (7), R-praziquantel

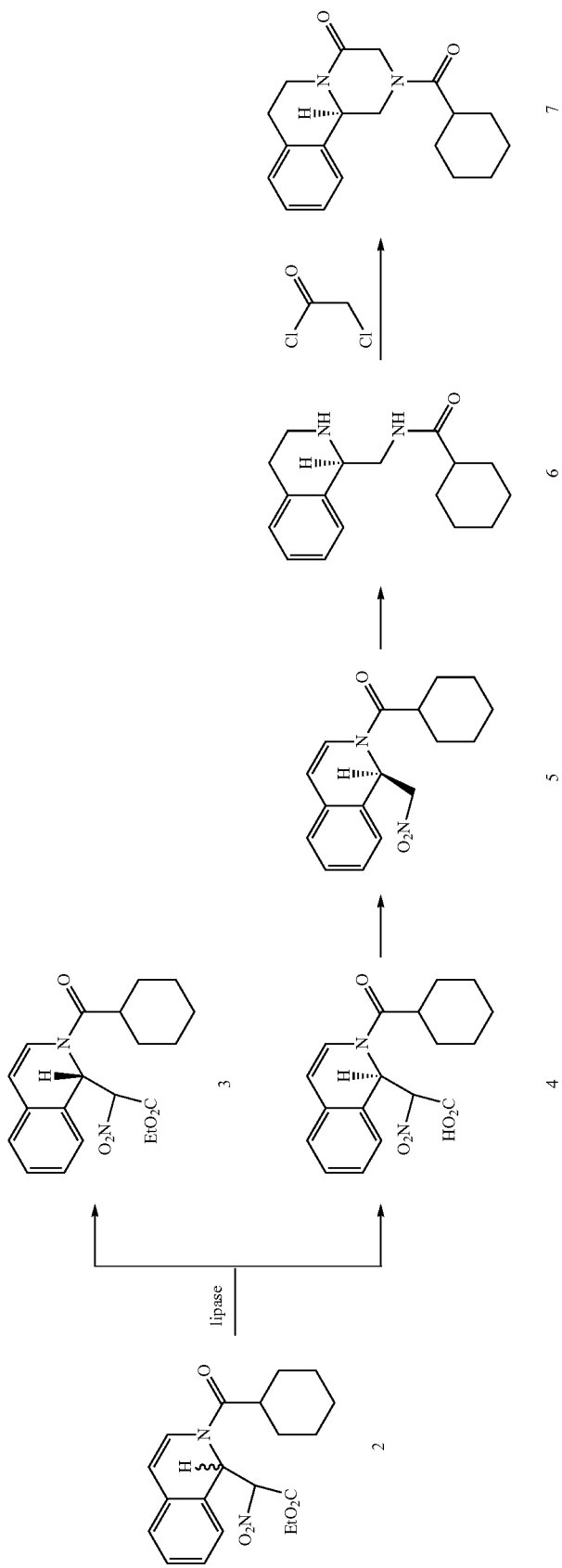

Preparation of compound of formula (5)

(i) The compound of formula (5) was prepared with *Thermomyces* lipase [*Thermomyces lanuginosus* lipase (SG165400, 100 u/mg, purchased from Guangzhou Howei Chemical Co., LTD)].

(1) Compound of formula (2) (i.e. nitromethane ethylester isoquinoline) (3.72 g, 10 mmol) and n-octane (3.72 g, 30 mmol) were dissolved in DMSO (20 ML), and the solution was added into phosphate buffer solution (40 mL, pH 7.8) with stirring under room temperature to obtain a mixed solution. *Thermomyces lanuginosus* lipase powder SG165400 (2 mg, 100 u/mg) was added to the mixed solution to start the reaction; after stirring for 16 hours under room temperature, the reaction was stopped when the hydrolysis reached 60%. Separation and purification through flash chromatography was carried out and 1.23 g of product, i.e. compound of formula (5), was obtained. Yield: 41%, ee value: 96%.

$^1$H NMR (CDCl$_3$, 400 MHz, δ ppm): 1.49-1.86 (m, 10H, 5xCH$_2$), 3.71-3.78 (m, 1H, CH), 4.42 (dd, 1H, CH$_2$), 4.74 (dd, 1H, CH$_2$), 5.38 (dd, 1H, CH), 6.01 (d, 1H, CH=CH), 6.58 (dd, 1H, CH=CH), 6.99-7.12 (m, 4H, ArH).

(2) Compound of formula (2) (i.e. nitromethane ethylester isoquinoline) (3.72 g, 10 mmol) and n-octane (3.72 g, 30 mmol) were dissolved in N-methyl-2-pyrrolidone (20 mL), and this solution was added into phosphate buffer solution (40 mL, pH 7.8) with stirring to obtain a mixed solution, to which *Thermomyces lanuginosus* lipase powder SG165400 (1 mg, 100 u/mg) was added to start the reaction. After stirring under 50° C. for 30 hours, the reaction was stopped when the hydrolysis reached 51%. Separation and purification through flash chromatography was carried out and 0.96 g product, i.e. compound of formula (5), was obtained. Yield: 32%, ee value: 91%.

$^1$H NMR (CDCl$_3$, 400 MHz, δ ppm): 1.49-1.86 (m, 10H, 5xCH$_2$), 3.71-3.78 (m, 1H, CH), 4.42 (dd, 1H, CH$_2$), 4.74 (dd, 1H, CH$_2$), 5.38 (dd, 1H, CH), 6.01 (d, 1H, CH=CH), 6.58 (dd, 1H, CH=CH), 6.99-7.12 (m, 4H, ArH).

(3) Compound of formula (2) (i.e. nitromethane ethylester isoquinoline) (3.72 g, 10 mmol) and n-octane (3.72 g, 30 mmol) were dissolved DMSO (20 mL), and this solution was added into phosphate buffer solution (40 mL, pH 7.8) with stirring to obtain a mixed solution, to which *Thermomyces lanuginosus* lipase powder SG165400 (4 mg, 100 u/mg) was added to start the reaction. After stirring under 75° C. for 4 hours, the reaction was stopped when the hydrolysis reached 51%. Separation and purification through flash chromatography was carried out and 1.2 g product, i.e. compound of formula (5), was obtained. Yield: 40%, ee value: 99%.

$^1$H NMR (CDCl$_3$, 400 MHz, δ ppm): 1.49-1.86 (m, 10H, 5xCH$_2$), 3.71-3.78 (m, 1H, CH), 4.42 (dd, 1H, CH$_2$), 4.74 (dd, 1H, CH$_2$), 5.38 (dd, 1H, CH), 6.01 (d, 1H, CH=CH), 6.58 (dd, 1H, CH=CH), 6.99-7.12 (m, 4H, ArH).

(ii) Preparation of compound of formula (5) with the lipase derived from *Candida rugosa* (SG061360, 2 u/mg, purchased from Guangzhou Howei Chemical Co., LTD)

(1) Compound of formula (2) (i.e. nitromethane ethylester isoquinoline) (1.86 g, 5 mmol) and n-octane (1.86 g, 15 mmol) were dissolved in DMSO (10 mL), and the solution was added into phosphate buffer solution (20 mL, pH 7.3) with stirring to obtain a mixed solution: to the mixed solution, the lipase powder (9 mg, 2 u/mg) was added to start the reaction; after stirring for 48 hours under room temperature, the reaction was stopped when the hydrolysis reached 31%. Separation and purification through flash chromatography was carried out and 0.42 g of product, i.e. compound of formula (5), was obtained. Yield: 28%, ee value: 73%.

$^1$H NMR (CDCl$_3$, 400 MHz, δ ppm): 1.49-1.86 (m, 10H, 5xCH$_2$), 3.71-3.78 (m, 1H, CH), 4.42 (dd, 1H, CH$_2$), 4.74 (dd, 1H, CH$_2$), 5.38 (dd, 1H, CH), 6.01 (d, 1H, CH=CH), 6.58 (dd, 1H, CH=CH), 6.99-7.12 (m, 4H, ArH).

(2) Compound of formula (2) (i.e. nitromethane ethylester isoquinoline) (1.86 g, 5 mmol) and n-octane (1.86 g, 15 mmol) were dissolved in acetonitrile (10 mL), and this solution was added into phosphate buffer solution (20 mL, pH 7.3) with stirring to obtain a mixed solution; to the mixed solution, the lipase powder (30 mg, 2 u/mg) was added to start the reaction: After stirring under 50° C. for 24 hours, the reaction was stopped when the hydrolysis reached 50%. Separation and purification through flash chromatography was carried out and 0.675 g product, i.e. compound of formula (5), was obtained. Yield: 45%, ee value: 91%.

$^1$H NMR (CDCl$_3$, 400 MHz, δ ppm): 1.49-1.86 (m, 10H, 5xCH$_2$), 3.71-3.78 (m, 1H, CH), 4.42 (dd, 1H, CH$_2$), 4.74 (dd, 1H, CH$_2$), 5.38 (dd, 1H, CH), 6.01 (d, 1H, CH=CH), 6.58 (dd, 1H, CH=CH), 6.99-7.12 (m, 4H, ArH).

(3) Compound of formula (2) (i.e. nitromethane ethylester isoquinoline) (1.86 g, 5 mmol) and n-octane (1.86 g, 15 mmol) were dissolved in DMSO (10 mL), and this solution was added into phosphate buffer solution (20 mL, pH 7.3) with stirring to obtain a mixed solution; to the mixed solution, the lipase powder (50 mg, 2 u/mg) was added to start the reaction; After stirring under 75° C. for 16 hours, the reaction was stopped when the hydrolysis reached 48%, Separation and purification through flash chromatography was carried out and 0.57 g product., i.e. compound of formula (5), was obtained. Yield: 38%, ee value: 87%.

$^1$H NMR (CDCl$_3$, 400 MHz, δ ppm): 1.49-1.86 (m, 10H, 5xCH$_2$), 3.71-3.78 (m, 1H, CH), 4.42 (dd, 1H, CH$_2$), 4.74 (dd, 1H, CH$_2$), 5.38 (dd, 1H, CH), 6.01 (d, 1H, CH=CH), 6.58 (dd, 1H, CH=CH), 6.99-7.12 (m, 4H, ArH).

(iii) Preparation of compound of formula (5) with the lipase derived from *Pseudomonas cepacia* (SG061357, 30 u/mg, purchased from Guangzhou Howei Chemical Co., LTD)

(1) Compound of formula (2) (i.e. nitromethane ethylester isoquinoline) (1.86 g, 5 mmol) and n-octane (1.86 g, 15 mmol) were dissolved in DMSO (10 mL), and the solution was added into phosphate buffer solution (20 mL, pH 7.0) with stirring to obtain a mixed solution; to the mixed solution, the lipase powder (3 mg, 30 u/mg) was added to start the reaction; after stirring for 36 hours under room temperature, the reaction was stopped when the hydrolysis reached 34%. Separation and purification through flash chromatography was carried out and 0.39 g of product, i.e. compound of formula (5), was obtained. Yield: 26%, ee value: 68%.

$^1$H NMR (CDCl$_3$, 400 MHz, δ ppm): 1.49-1.86 (m, 10H, 5xCH$_2$), 3.71-3.78 (m, 1H, CH), 4.42 (dd, 1H, CH$_2$), 4.74 (dd, 1H, CH$_2$), 5.38 (dd, 1H, CH), 6.01 (d, 1H, CH=CH), 6.58 (dd, 1H, CH=CH), 6.99-7.12 (m, 4H, ArH).

(2) Compound of formula (2) (i.e. nitromethane ethylester isoquinoline) (1.86 g, 5 mmol) and n-octane (1.86 g, 15 mmol) were dissolved in 1,4-dioxane (10 mL), and the solution was added into phosphate buffer solution (20 mL, pH 7.0)

with stirring to obtain a mixed solution; to the mixed solution, the lipase powder (10 mg, 30 u/mg) was added to start the reaction; after stirring under 50° C. for 20 hours, the reaction was stopped when the hydrolysis reached 48%. Separation and purification through flash chromatography was carried out and 0.645 g of product, i.e. compound of formula (5), was obtained. Yield: 43%, ee value: 88%.

$^1$H NMR (CDCl$_3$, 400 MHz, δ ppm): 1.49-1.86 (m, 10H, 5xCH$_2$), 3.71-3.78 (m, 1H, CH), 4.42 (dd, 1H, CH$_2$), 4.74 (dd, 1H, CH$_2$), 5.38 (dd, 1H, CH), 6.01 (d, 1H, CH=CH), 6.58 (dd, 1H, CH=CH), 6.99-7.12 (m, 4H, ArH).

(3) Compound of formula (2) (i.e. nitromethane ethylester isoquinoline) (1.86 g, 5 mmol) and n-octane (1.86 g, 15 mmol) were dissolved in DMSO (10 mL), and the solution was added into phosphate buffer solution (20 mL, pH 7.0) with stirring to obtain a mixed solution; to the mixed solution, the lipase powder (20 mg, 30 u/mg) was added to start the reaction; after stirring under 75° C. for 6 hours, the reaction was stopped when the hydrolysis reached 49%. Separation and purification through flash chromatography was carried out and 0.645 g of product, i.e. compound of formula (5), was obtained. Yield: 43%, ee value: 88%.

$^1$H NMR (CDCl$_3$, 400 MHz, δ ppm): 1.49-1.86 (m, 10H, 5xCH$_2$), 3.71-3.78 (m, 1H, CH), 4.42 (dd, 1H, CH$_2$), 4.74 (dd, 1H, CH$_2$), 5.38 (dd, 1H, CH), 6.01 (d, 1H, CH=CH), 6.58 (dd, 1H, CH=CH), 6.99-7.12 (m, 4H, ArH).

(iv) Preparation of compound of formula (5) with the lipase derived from *Pseudomonas fluorescens* (SG075907, 40 u/mg, purchased from Guangzhou Howei Chemical Co., LTD)

(1) Compound of formula (2) (i.e. nitromethane ethylester isoquinoline) (1.86 g, 5 mmol) and n-octane (1.86 g, 15 mmol) were dissolved in DMSO (10 mL), and the solution was added into phosphate buffer solution (20 mL, pH 7.2) with stirring to obtain a mixed solution; to the mixed solution, the lipase powder (3 mg, 40 u/mg) was added to start the reaction; after stirring for 36 hours under room temperature, the reaction was stopped when the hydrolysis reached 46%. Separation and purification through flash chromatography was carried out and 0.525 g of product, i.e. compound of formula (5), was obtained. Yield: 35%, ee value: 80%.

$^1$H NMR (CDCl$_3$, 400 MHz, δ ppm): 1.49-1.86 (m, 10H, 5xCH$_2$), 3.71-3.78 (m, 1H, CH), 4.42 (dd, 1H, CH$_2$), 4.74 (dd, 1H, CH$_2$), 5.38 (dd, 1H, CH), 6.01 (d, 1H, CH=CH), 6.58 (dd, 1H, CH=CH), 6.99-7.12 (m, 4H, ArH).

(2) Compound of formula (2) (i.e. nitromethane ethylester isoquinoline) (1.86 g, 5 mmol) and n-octane (1.86 g, 15 mmol) were dissolved in N-methyl-2-pyrrolidone (10 mL), and the solution was added into phosphate buffer solution (20 mL, pH 7.2) with stirring to obtain a mixed solution; to the mixed solution, the lipase powder (10 mg, 40 u/mg) was added to start the reaction; after stirring under 50° C. for 13 hours, the reaction was stopped when the hydrolysis reached 48%. Separation and purification through flash chromatography was carried out and 0.465 g of product, i.e. compound of formula (5), was obtained. Yield: 31%, ee value: 97%.

$^1$H NMR (CDCl$_3$, 400 MHz, δ ppm): 1.49-1.86 (m, 10H, 5xCH$_2$), 3.71-3.78 (m, 1H, CH), 4.42 (dd, 1H, CH$_2$), 4.74 (dd, 1H, CH$_2$), 5.38 (dd, 1H, CH), 6.01 (d, 1H, CH=CH), 6.58 (dd, 1H, CH=CH), 6.99-7.12 (m, 4H, ArH).

(3) Compound of formula (2) (i.e. nitromethane ethylester isoquinoline) (1.86 g, 5 mmol) and n-octane (1.86 g, 15 mmol) were dissolved in DMSO (10 mL), and the solution was added into phosphate buffer solution (20 mL, pH 7.2) with stirring to obtain a mixed solution; to the mixed solution, the lipase powder (20 mg, 40 u/mg) was added to start the reaction; after stirring under 75° C. for 3 hours, the reaction was stopped when the hydrolysis reached 53%. Separation and purification through flash chromatography was carried out and 0.39 g of product, i.e. compound of formula (5), was obtained. Yield: 26%, ee value: 69%.

$^1$H NMR (CDCl$_3$, 400 MHz, δ ppm): 1.49-1.86 (m, 10H, 5xCH$_2$), 3.71-3.78 (m, 1H, CH), 4.42 (dd, 1H, CH$_2$), 4.74 (dd, 1H, CH$_2$), 5.38 (dd, 1H, CH), 6.01 (d, 1H, CH=CH), 6.58 (dd, 1H, CH=CH), 6.99-7.12 (m, 4H, ArH).

(v) Preparation of compound of formula (5) with *Candida antarctica* lipase (SG063906, 1 u/mg, purchased from Guangzhou Howei Chemical Co., LTD)

(1) Compound of formula (2) (i.e. nitromethane ethylester isoquinoline) (1.86 g, 5 mmol) and n-octane (1.86 g, 15 mmol) were dissolved in N-methyl-2-pyrrolidone (10 mL), and the solution was added into phosphate buffer solution (20 mL, pH 7.2) with stirring to obtain a mixed solution; to the mixed solution, the lipase powder (18 mg, 1 u/mg) was added to start the reaction; after stirring for 48 hours under room temperature, the reaction was stopped when the hydrolysis reached 36%. Separation and purification through flash chromatography was carried out and 0.48 g of product, i.e. compound of formula (5), was obtained. Yield: 32%, ee value: 93%.

$^1$H NMR (CDCl$_3$, 400 MHz, δ ppm): 1.49-1.86 (m, 10H, 5xCH$_2$), 3.71-3.78 (m, 1H, CH), 4.42 (dd, 1H, CH$_2$), 4.74 (dd, 1H, CH$_2$), 5.38 (dd, 1H, CH), 6.01 (d, 1H, CH=CH), 6.58 (dd, 1H, CH=CH), 6.99-7.12 (m, 4H, ArH).

(2) Compound of formula (2) (i.e. nitromethane ethylester isoquinoline) (1.86 g, 5 mmol) and n-octane (1.86 g, 15 mmol) were dissolved in DMSO (10 mL), and the solution was added into phosphate buffer solution (20 mL, pH 7.2) with stirring to obtain a mixed solution; to the mixed solution, the lipase powder (39 mg, 1 u/mg) was added to start the reaction; after stirring under 50° C. for 48 hours, the reaction was stopped when the hydrolysis reached 50%. Separation and purification through flash chromatography was carried out and 0.57 g of product, i.e. compound of formula (5), was obtained. Yield: 38%, ee value: 95%.

$^1$H NMR (CDCl$_3$, 400 MHz, δ ppm): 1.49-1.86 (m, 10H, 5xCH$_2$), 3.71-3.78 (m, 1H, CH), 4.42 (dd, 1H, CH$_2$), 4.74 (dd, 1H, CH$_2$), 5.38 (dd, 1H, CH), 6.01 (d, 1H, CH=CH), 6.58 (dd, 1H, CH=CH), 6.99-7.12 (m, 4H, ArH).

(3) Compound of formula (2) (i.e. nitromethane ethylester isoquinoline) (1.86 g, 5 mmol) and n-octane (1.86 g, 15 mmol) were dissolved in acetonitrile (10 mL), and the solution was added into phosphate buffer solution (20 mL, pH 7.2) with stirring to obtain a mixed solution; to the mixed solution, the lipase powder (55 mg, 1 u/mg) was added to start the reaction; after stirring under 75° C. for 35 hours, the reaction was stopped when the hydrolysis reached 50%. Separation and purification through flash chromatography was carried out and 0.63 g of product, i.e. compound of formula (5), was obtained. Yield: 42%, ee value: 96%.

$^1$H NMR (CDCl$_3$, 400 MHz, δ ppm): 1.49-1.86 (m, 10H, 5xCH$_2$), 3.71-3.78 (m, 1H, CH), 4.42 (dd, 1H, CH$_2$), 4.74 (dd, 1H, CH$_2$), 5.38 (dd, 1H, CH), 6.01 (d, 1H, CH=CH), 6.58 (dd, 1H, CH=CH), 6.99-7.12 (m, 4H, ArH).

Preparation of compound of formula (6)

(1) Compound of formula (5) (3 g, 0.01 mot), absolute methanol (60 mL) and 5% Ru containing catalyst Ru/C (0.2 g) were added into a sealed container. After the air in the container was replaced with hydrogen, hydrogen (1.5 MPa) was fed; the reaction was heated to 35-45° C. and stirred for 6-8 hours. When the reaction was indicated as complete, the catalyst was filtered and recovered; the reaction liquid was concentrated under reduced pressure and the residue was separated and purified through flash chromatography to obtain compound of formula (6) as solid, which was recrystallized with ethyl ether/n-hexane to obtain 2.4 g pure product, i.e. compound of formula (6), as light yellow crystal. Yield: 86%, melting point: 111-112° C., ee value: >99%.
$^1$H NMR (400 MHz, CDCl$_3$): δ 1.16-1.27 (m, 4H, CH$_2$), 1.35-1.47 (m, 2H, CH$_2$), 1.64-1.85 (m, 4H, CH$_2$), 2.73-2.85 (m, 2H, CH$_2$), 3.03-3.06 (m, 1H, CH$_2$), 3.13-3.18 (m, 1H, CH$_2$), 3.32-3.37 (m, 1H, CH$_2$), 3.52-3.62 (m, 1H, CH$_2$), 3.73-3.81 (m, 1H, CH$_2$), 4.10 (dd, 1H, CH), 6.30 (br s, 1H, NH), 7.08-7.20 (m, 4H, Ar-H), MS (ESI+ve): m/z: 273 [M+H]$^+$.

(2) Compound of formula (5) (3 g, 0.01 mol), absolute ethanol (60 mL) and 10% Pd containing catalyst Pd/C (0.3 g) were added into a sealed container. After the air in the container was replaced with hydrogen, hydrogen (3 Mpa) was fed, the reaction was heated to 45-50° C. and was stirred for 12 hours. When the reaction was indicated as complete, the catalyst was filtered and recovered; the reaction liquid was concentrated under reduced pressure and the residue was separated and purified through flash chromatography to obtain compound of formula (6) as solid, which was recrystallized with ethyl ether/n-hexane to obtain 0.22 g pure product, i.e. compound of formula (6), as light yellow crystal. Yield: 81%, melting point: 111-112° C., ee value: >99%.
$^1$H NMR (400 MHz, CDCl$_3$): δ 1.16-1.27 (m, 4H, CH$_2$), 1.35-1.47 (m, 2H, CH$_2$), 1.64-1.85 (m, 4H, CH$_2$), 2.73-2.85 (m, 2H, CH$_2$), 3.03-3.06 (m, 1H, CH$_2$), 3.13-3.18 (m, 1H, CH$_2$), 3.32-3.37 (m, 1H, CH$_2$), 3.52-3.62 (m, 1H, CH$_2$), 3.73-3.81 (m, 1H, CH$_2$), 4.10 (dd, 1H, CH), 6.30 (br s, 1H, NH), 7.08-7.20 (m, 4H, Ar-H), MS (ESI+ve): m/z: 273 [M+H]$^+$.

Preparation of compound of formula (7), R-praziquantel (1) Compound of formula (6) (0.27 g, 1 mmol) was dissolved in dichloromethane (20 mL), prior to further addition of 50% by mass of sodium hydroxide solution (0.48 mL, 6 mmol), and then a solution of chloroacetyl chloride (0.13 g, 1.1 mmol) in 10 mL dichloromethane was added dropwise with the temperature of the reaction mixture controlled at room temperature; after the addition, the stirring was continued for another 1 hour. HPLC indicated that the reaction was complete; to the reaction mixture, the catalyst benzyltriethylammonium chloride (22.7 mg, 0.1 mmol) was added, and the reaction mixture was heated to reflux for 4-5 hours. HPLC indicated that the reaction was complete; the reaction mixture was poured into 10 mL of ice water and the organic phase was extracted with dichloromethane (10 mL×2) before being washed with water (2 ×2 mL), 5% HCl (2 mL) and again water (2 mL), and then dried with anhydrous sodium sulfate; the organic phase was subjected to rotary evaporation to remove the solvent, and the residue was moved onto gel column chromatography (chloroform/methanol=98:2) to obtain 0.25 g of object product, R-praziquantel, i.e. compound of formula (7). Yield: 80%, melting point: 113-115° C., ee value: 99%.
$^1$H NMR (400 MHz, CDCl$_3$): δ 1.21-1.96 (m, 10H, 5xCH$_2$), 2.45-2.50 (m, 1H, CH), 2.78-3.05 (m, 4H, CH$_2$), 4.10 (d, 1H, CH$_2$), 4.48 (d, 1H, CH$_2$), 4.79-4.85 (m, 2H, CH$_2$), 5.20 (d, 1H, CH), 7.12-7.30 (m, 4H, Ar-H). MS (ESI+ve): m/z: 313 [M+H]$^+$.

(2) Compound of formula (6) (8.1 g, 30 mmol) was dissolved in methyl tert-butyl ether (100 mL) prior to further addition of 50% by mass of sodium hydroxide solution (14.5 mL, 180 mmol), and then a solution of chloroacetyl chloride (3.9 g, 33 mmol) in 20 mL methyl tert-butyl ether was added dropwise with the temperature of the reaction mixture controlled at room temperature; after the addition, the stirring was continued for another 1 hour. HPLC indicated that the reaction was complete: to the reaction mixture, the catalyst benzyltriethylammonium chloride (0.68 g, 3 mmol) was added, and the reaction mixture was heated to reflux for 7-8 hours, and HPLC indicated that the reaction was complete; the reaction mixture was poured into 200 mL of ice water and the organic phase was extracted with methyl tert-butyl ether (100 mL+2) before being washed with water (2+60 mL), 5% HCl (60 mL) and again water (60 mL), and then dried with anhydrous sodium sulfate; the organic phase was subjected to rotary evaporation to remove the solvent, and the residue was moved onto gel column chromatography (chloroform/methanol=98: 2) to obtain 7.6 g of object product, R-praziquantel, i.e. compound of formula (7). Yield: 81%, melting point: 113-115° C., ee value: 99%.
$^1$H NMR (400 MHz, CDCl$_3$): δ 1.21-1.96 (m, 10H, 5xCH$_2$), 2.45-2.50 (m, 1H, CH), 2.78-3.05 (m, 4H, CH$_2$), 4.10 (d, 1H, CH$_2$), 4.48 (d, 1H, CH$_2$), 4.79-4.85 (m, 2H, CH$_2$), 5.20 (d, 1H, CH), 7.12-7.30 (m, 4H, Ar-H). MS (ESI+ve): m/z: 313 [M+H]$^+$.

Example 2

I. Preparation of Compound of Formula (8)

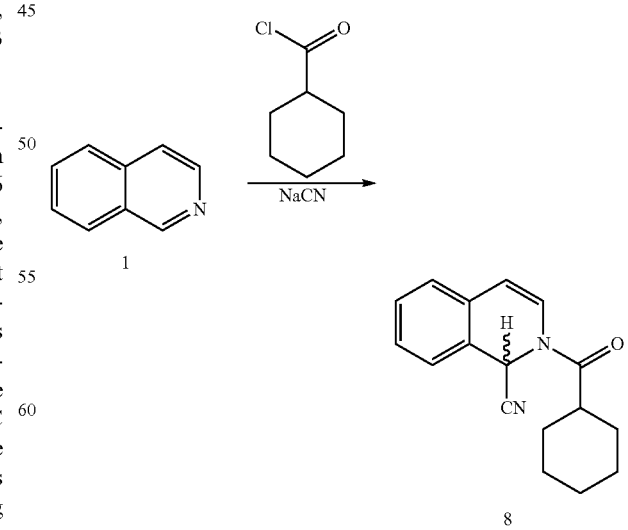

Compound of formula (1) (i.e. isoquinoline) (42.62, 0.33 mol) and potassium cyanide (26.04 g, 0.4 mol) were dissolved in 300 mL of water, then followed by further addition of cyclohexanoyl chloride (58.05 g, 0.4 mol) dropwise under vigorously stirring, and the temperature of the reaction mixture was no higher than −10° C.; after the addition, the stirring was continued at a temperature below 0° C. for 4 hours; HPLC indicated that the reaction was completed, and the water phase was extracted with dichloromethane (400 mL), The combined organic phase was washed with saturated saline solution, 10% HCl, saturated saline solution and 5% KOH, and finally saturated saline solution. The organic phase was dried with anhydrous magnesium sulfate, filtered to remove the desiccant, and concentrated under reduced pressure to obtain 79.8 g of compound of formula (8) as yellow solid. Yield: 91%, melting point: 126-127° C.

$^1$H NMR (400 MHz, CDCl$_3$): δ 1.32-1.86 (m, 10H, 5xCH$_2$), 2.35 (dd, 1H, CH), 6.08 (d, 1H, CH), 6.58 (s, 1H, CH), 6.65 (s, 1H, CH), 7.12-7.31 (m, 4H, Ar-H). MS (ESI, +ve): m/z: 267 [M+H]$^+$.

II. Preparation of R-praziquantel

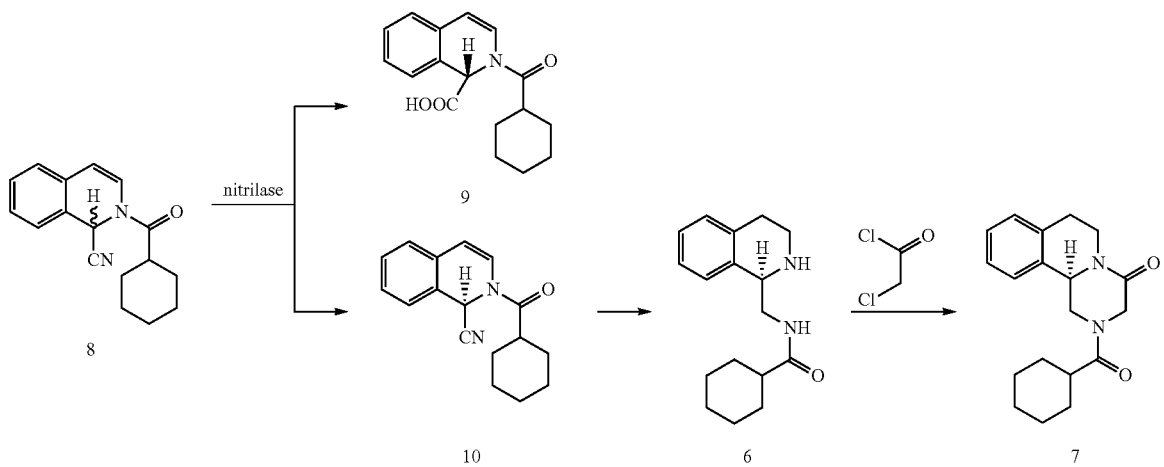

(i) Preparation of compound of formula (10)
(1) Preparation of compound of formula (10) with the nitrilase derived from *Arabidopsis* (*Arabidopsis thaliana* NIT, Lonza Corporation, Switzerland)

(1) To a reactor, compound of formula (8) (2.7 g, 10 mmol) and potassium phosphate buffer solution (122 mL, 50 mM, pH 7.5, containing 5 mM of DTT and 1 mM of EDTA) were added, and the nitrilase (13.5 mg, derived from *Arabidopsis, Arabidopsis thaliana* NIT, Lonza Corporation, Switzerland) was added to start the reaction. The reaction was carried out at a system temperature of 5° C. under stirring, monitored by HPLC. After reacting for 12-13 hours, the reaction was stopped, and the product therefrom was extracted with ethyl acetate (4×50 mL). The residue was concentrated under reduced pressure and moved on gel column chromatography (ethyl acetate: n-hexane=1:20) to obtain 1.1 g of product, i.e. compound of formula (10), as oil. Yield: 41%, ee value: 99%.

$^1$H NMR (400 MHz, CDCl$_3$): δ 1.32-1.86 (m, 10H, 5xCH$_2$), 2.35 (dd, 1H, CH), 6.08 (d, 1H, CH), 6.58 (s, 1H, CH), 6.65 (s, 1H, CH), 7.12-7.31 (m, 4H, Ar-H). MS (ESI, +ve): m/z: 267 [M+H]$^+$.

(2) To a reactor, compound of formula (8) (2.7 g, 10 mmol) and potassium phosphate buffer solution (122 mL, 50 mM, pH 7.5, containing 5 mM of DTT and 1 mM of EDTA) were added, and the nitrilase (50 mg, derived from *Arabidopsis, Arabidopsis thaliana* NIT, Lonza Corporation, Switzerland) was added to start the reaction. The reaction was carried out at a system temperature of 50° C. under stirring, monitored by HPLC. After reacting for 6-8 hours, the reaction was stopped, and the product therefrom was extracted with ethyl acetate (4×50 mL). The residue was concentrated under reduced pressure and moved on gel column chromatography (ethyl acetate: n-hexane=1:20) to obtain 1.08 g of product, i.e. compound of formula (10), as oil. Yield: 40%, ee valve: 98%.

$^1$H NMR (400 MHz, CDCl$_3$): δ 1.32-1.86 (m, 10H, 5xCH$_2$), 2.35 (dd, 1H, CH), 6.08 (d, 1H, CH), 6.58 (s, 1H, CH), 6.65 (s, 1H, CH), 7.12-7.31 (m, 4H, Ar-H). MS (ESI, +ve): m/z: 267 [M+H]$^+$.

(3) To a reactor, compound of formula (8) (2.7 g, 10 mmol) and potassium phosphate buffer solution (122 mL, 50 mM, pH 7.5, containing 5 mM of DTT and 1 mM of EDTA) were added, and the nitrilase (35 mg, derived from *Arabidopsis, Arabidopsis thaliana* NIT, Lonza Corporation, Switzerland) was added to start the reaction. The reaction was carried out at a system temperature of 75° C. under stirring, monitored by HPLC. After reacting for 7-8 hours, the reaction was stopped, and the product therefrom was extracted with ethyl acetate (4×50 mL). The residue was concentrated under reduced pressure and moved on gel column chromatography (ethyl acetate: n-hexane=1:20) to obtain 1 g of product, i.e. compound of formula (10), as oil. Yield: 40%, ee value: 98%.

$^1$H NMR (400 MHz, CDCl$_3$): δ 1.32-1.86 (m, 10H, 5xCH$_2$), 2.35 (dd, 1H, CH), 6.08 (d, 1H, CH), 6.58 (s, 1H, CH), 6.65 (s, 1H, CH), 7.12-7.31 (m, 4H, Ar-H). MS (ESI, +ve): m/z: 267 [M+H]$^+$.

(2) Preparation of compound of formula (10) with nitrilases derived from fungi.

(1) To a reactor, compound of formula (8) (2.7 g, 10 mmol) and potassium phosphate buffer solution (100 mL, 50 mM, pH 7.5, containing 5 mM of DTT and 1 mM of EDTA) were added, and the nitrilase from *Aspergillus niger* (15 mg, *Aspergillus niger* K10, DSMZ) was added to start the reaction. The reaction was carried out at a system temperature of 5° C. under stirring, monitored by HPLC. After reacting for 15-16 hours, the reaction was stopped, and the product therefrom was extracted with ethyl acetate (4×50 mL). The residue was concentrated under reduced pressure and moved on gel column chromatography (ethyl acetate:n-hexane=1:20) to obtain 0.756 g of product, i.e. compound of formula (10), as oil. Yield: 28%, ee value: 91%.
$^1$H NMR (400 MHz, CDCl$_3$): δ 1.32-1.86 (m, 10H, 5xCH$_2$), 2.35 (dd, 1H, CH), 6.08 (d, 1H, CH), 6.58 (s, 1H, CH), 6.65 (s, 1H, CH), 7.12-7.31 (m, 4H, Ar-H). MS (ESI, +ve): m/z: 267 [M+H]$^+$.

(2) To a reactor, compound of formula (8) (5.4 g, 20 mmol) and potassium phosphate buffer solution (220 mL, 50 mM, pH 7.5, containing 5 mM of DTT and 1 mM of EDTA) were added, and the nitrilase from *Aspergillus niger* (100 mg, *Aspergillus niger* K10, DSMZ) was added to start the reaction. The reaction was carried out at a system temperature of 50° C. under stirring, monitored by HPLC. After reacting for 6-7 hours the reaction was stopped, and the product therefrom was extracted with ethyl acetate (4×50 The residue was concentrated under reduced pressure and moved on gel column chromatography (ethyl acetate:n-hexane=1:20) to obtain 2.32 g of product, i.e. compound of formula (10), as oil. Yield: 43%, ee value: 97%.
$^1$H NMR (400 MHz, CDCl$_3$): δ 1.32-1.86 (m, 10H, 5xCH$_2$), 2.35 (dd, 1H, CH), 6.08 (d, 1H, CH), 6.58 (s, 1H, CH), 6.65 (s, 1H, CH), 7.12-7.31 (m, 4H, Ar-H). MS (ESI, +ve): m/z: 267 [M+H]$^+$.

(3) To a reactor, compound of formula (8) (5.4 g, 20 mmol) and potassium phosphate buffer solution (220 mL, 50 mM, pH 7.5, containing 5 mM of DTT and 1 mM of EDTA) were added, and the nitrilase from *Aspergillus niger* (150 mg, *Aspergillus niger* K10, DSMZ) was added to start the reaction. The reaction was carried out at a system temperature of 75° C. under stirring, monitored by HPLC. After reacting for 4-5 hours, the reaction was stopped, and the product therefrom was extracted with ethyl acetate (4×50 mL). The residue was concentrated under reduced pressure and moved on gel column chromatography (ethyl acetate:n-hexane=1:20) to obtain 1.73 g of product, i.e. compound of formula (10), as oil. Yield: 32%, ee value: 87%.
$^1$H NMR (400 MHz, CDCl$_3$): δ 1.32-1.86 (m, 10H, 5xCH$_2$), 2.35 (dd, 1H, CH), 6.08 (d, 1H, CH), 6.58 (s, 1H, CH), 6.65 (s, 1H, CH), 7.12-7.31 (m, 4H, Ar-H). MS (ESI, +ve): m/z: 267 [M+H]$^+$.

(3) Preparation of compound of formula (10) with nitrilases from bacteria (1) To a reactor, compound of formula (8) (2.7 g, 10 mmol) and potassium phosphate buffer solution (122 mL, 50 mM, pH 7.5, containing 5 mM of DTT and 1 mM of EDTA) were added, and the nitrilase from *Alcaligenes faecalis* (27 mg, *Alcaligenes faecalis*, American Type Culture Collection (ATCC)) was added to start the reaction. The reaction was carried out at a system temperature of 5° C. under stirring, monitored by HPLC. After reacting for 15-16 hours, the reaction was stopped, and the product therefrom was extracted with ethyl acetate (4×50 mL). The residue was concentrated under reduced pressure and moved on gel column chromatography (ethyl acetate:n-hexane=1:20) to obtain 1.1 g of product, i.e. compound of formula (10), as oil. Yield: 41%, ee value: 99%.
$^1$H NMR (400 MHz, CDCl$_3$): δ 1.32-1.86 (m, 10H, 5xCH$_2$), 2.35 (dd, 1H, CH), 6.08 (d, 1H, CH), 6.58 (s, 1H, CH), 6.65 (s, 1H, CH), 7.12-7.31 (m, 4H, Ar-H). MS (ESI, +ve): m/z: 267 [M+H]$^+$.

(2) To a reactor, compound of formula (8) (5.4 g, 20 mmol) and potassium phosphate buffer solution (220 mL, 50 mM, pH 7.5, containing 5 mM of DTT and 1 mM of EDTA) were added, and the nitrilase from *Alcaligenes faecalis* (110 mg, *Alcaligenes faecalis*, American Type Culture Collection (ATCC)) was added to start the reaction. The reaction was carried out at a system temperature of 50° C. under stirring, monitored by HPLC. After reacting for 6-7 hours, the reaction was stopped, and the product therefrom was extracted with ethyl acetate (4×50 mL). The residue was concentrated under reduced pressure and moved on gel column chromatography (ethyl acetate:n-hexane=1:20) to obtain 2.4 g of product, i.e. compound of formula (10), as oil, Yield: 43%, ee value: 99%.
$^1$H NMR (400 MHz, CDCl$_3$): δ 1.32-1.86 (m, 10H, 5xCH$_2$), 2.35 (dd, 1H, CH), 6.08 (d, 1H, CH), 6.58 (s, 1H, CH), 6.65 (s, 1H, CH), 7.12-7.31 (m, 4H, Ar-H). MS (ESI, +ve): m/z: 267 [M+H]$^+$.

(3) To a reactor, compound of formula (8) (5.4 g, 20 mmol) and potassium phosphate buffer solution (220 mL, 50 mM, pH 7.5, containing 5 mM of DTT and 1 mM of EDTA) were added, and the nitrilase (150 mg, *Alcaligenes faecalis*, American Type Culture Collection (ATCC)) was added to start the reaction. The reaction was carried out at a system temperature of 75° C. under stirring, monitored by HPLC. After reacting for 10-11 hours, the reaction was stopped, and the product therefrom was extracted with ethyl acetate (4×50 mL). The residue was concentrated under reduced pressure and moved on gel column chromatography (ethyl acetate:n-hexane=1: 20) to obtain 1.89 g of product, i.e. compound of formula (10), as oil. Yield: 35%, ee value: 88%.
$^1$H NMR (400 MHz, CDCl$_3$): δ 1.32-1.86 (m, 10H, 5xCH$_2$), 2.35 (dd, 1H, CH), 6.08 (d, 1H, CH), 6.58 (s, 1H, CH), 6.65 (s, 1H, CH), 7.12-7.31 (m, 4H, Ar-H). MS (ESI, +ve): m/z: 267 [M+H]$^+$.

(ii) Preparation of compound of formula (6)

(1) To an sealed container, compound of formula (10) (3 g, 0.01 mol), absolute methanol (60 mL) and 5% Ru containing catalyst Ru/C (0.2 g) were added. After the air in the container was replaced with hydrogen, hydrogen (1.5 Mpa) was fed, the reaction was heated to 45 - 50° C. and was stirred for 6-8 hours. When the reaction was indicated as complete, the catalyst was filtered and recovered. The reaction liquid was concentrated under reduced pressure and the residue was separated and purified through flash chromatography to obtain solid compound 7, which was recrystallized with ethyl ether/n-hexane to obtain 2.4 g of pure product, i.e. compound of formula (6), as light yellow crystal. Yield: 86%, melting point: 111-112° C., ee value: >99%.
$^1$H NMR (400 MHz, CDCl$_3$): δ 1.16-1.27 (m, 4H, CH$_2$), 1.35-1.47 (m, 2H, CH$_2$), 1.64-1.85 (m, 4H, CH$_2$), 2.73-2.85 (m, 2H, CH$_2$), 3.03-3.06 (m, 1H, CH$_2$), 3.13-3.18 (m, 1H, CH$_2$), 3.32-3.37 (m, 1H, CH$_2$), 3.52-3.62 (m, 1H, CH$_2$), 3.73-3.81 (m, 1H, CH$_2$), 4.10 (dd, 1H, CH), 6.30 (br s, 1H, NH), 7.08-7.20 (m, 4H, Ar-H), MS (ESI+ve): m/z: 273 [M+H]$^+$.

(2) To an sealed container, compound of formula (10) (27 g, 0.1 mol), absolute ethanol (380 mL) and 10% Pd/C catalyst (0.3 g) were added. After the air in the sealed container was replaced with hydrogen, hydrogen (3 Mpa) was fed, the reaction was heated to 45-50° C. and was stirred for 12-13 hours. When the reaction was indicated as complete, the catalyst was filtered and recovered. The reaction liquid was concentrated under reduced pressure and the residue was separated and purified through flash chromatography to obtain solid compound 7, which was recrystallized with ethyl ether/n-hexane to obtain 22 g of pure product, i.e. compound of formula (6), as light yellow crystal. Yield: 81%, melting point: 111-112° C., ee value: >99%.
$^1$H NMR (400 MHz, CDCl$_3$): δ 1.16-1.27 (m, 4H, CH$_2$), 1.35-1.47 (m, 2H, CH$_2$), 1.64-1.85 (m, 4H, CH$_2$), 2.73-2.85 (m, 2H, CH$_2$), 3.03-3.06 (m, 1H, CH$_2$), 3.13-3.18 (m, 1H, CH$_2$), 3.32-3.37 (m, 1H, CH$_2$), 3.52-3.62 (m, 1H, CH$_2$), 3.73-3.81 (m, 1H, CH$_2$), 4.10 (dd, 1H, CH), 6.30 (br s, 1H, NH), 7.08-7.20 (m, 4H, Ar-H), MS (ESI+ve): m/z: 273 [M+H]$^+$.

(iii) Preparation of R-praziquantel (7)

(1) To a reactor, compound of formula (6) (2.7 g, 10 mmol) prepared by the method described above, ethyl acetate (30 mL) and anhydrous potassium carbonate (3.2 g, 23 mmol) were added and stirred well. Chloroacetyl chloride (1.4 g, 12 mmol) was added into this reaction mixture dropwise prior to stirring under room temperature for 3 hours. HPLC indicated the reaction was completed. To the reaction mixture, benzyltriethylammonium chloride (22.7 mg, 0.1 mmol) was added and the reaction was heated to reflux for 6-8 hours, and HPLC indicated the reaction was completed. After filtration to remove insoluble substances, the ethyl acetate layer was washed with water and saturated saline solution successively, dried with anhydrous magnesium sulfate, and then solvents were removed under reduced pressure to give a crude product. The crude product was recrystallized with absolute ethanol to obtain 2.4 g of a pure product R-praziquantel, i.e. compound of formula (7). Yield; 78%, melting point: 113 115° C., ee value: >99%.

$^1$H NMR (400 MHz, CDCl3): δ 1.21-1.96 (m, 10H, 5xCH2), 2.45-2.50 (m, 1H, CH), 2.78-3.05 (m, 4H, CH2), 4.10 (d, 1H, CH2), 4.48 (d, 1H, CH2), 4.79-4.85 (m, 2H, CH2), 5.20 (d, 1H, CH), 7.12-7.30 (m, 4H, Ar-H). MS (ESI, +ve): m/z: 313 [M+H]$^+$.

(2) To a reactor, compound of formula (6) (54 g, 200 mmol) prepared by the method described above, dichloroethane (500 mL) and anhydrous potassium carbonate (65 g, 460 mmol) were added and stirred well. Chloroacetyl chloride (28 g, 240 mmol) was added into this reaction mixture dropwise prior to stirring under room temperature for 5-6 hours, till HPLC indicated the reaction was completed. To the reaction mixture, benzyltriethylammonium chloride (454 mg, 2 mmol) was added and then the reaction was heated to reflux for 10-12 hours, till HPLC indicated the reaction was completed. After filtration to remove insoluble substances, the ethyl acetate layer was washed with water and saturated saline solution successively, dried with anhydrous magnesium sulfate, and then the solvents were removed under reduced pressure to give a crude product. The crude product was recrystallized with absolute ethanol to obtain 50 g of a pure product R-praziquantel, i.e. compound of formula (7). Yield; 80%, melting point; 113-115° C., ee value: >99%.

$^1$H NMR (400 MHz, CDCl3): δ 1.21-1.96 (m, 10H, 5xCH2), 2.45-2.50 (m, 1H, CH), 2.78-3.05 (m, 4H, CH2), 4.10 (d, 1H, CH2), 4.48 (d, 1H, CH2), 4.79-4.85 (m, 2H, CH2), 5.20 (d, 1H, CH), 7.12-7.30 (m, 4H, Ar-H). MS (ESI, +ve): m/z: 313 [M+H]$^+$.

Example 3

In this example, a method is provided for preparing an intermediate (6) of R-praziquantel.

To a reactor, compound (11) (2.7 g, 10 mmol), compound (12) (1.35 g, 6.56 mmol) and toluene (50 mL, containing 20 mg of water) were added and stirred well before adding 6 mg of CAL-A (6000 u/g, L3420, Sigma) to start the reaction. The reaction was carried out under a temperature of 30° C. with stirring, monitored by HPLC and stopped after reacting for 46-48 hours. The resulting mixture was filtered to remove enzymes, washed with 10 mL of toluene, and the organic layer was concentrated under reduced pressure. The residues were separated through silica gel column chromatography (ethyl acetate/n-hexane=1:15) to obtain 1.16 g of intermediate (6). Yield: 43%, melting point: 111-112° C., ee value: >99%.

NMR data of intermediate (6): $^1$H NMR (400 MHZ, CDCl$_3$): δ 1.16-1.27 (m, 4H, CH$_2$), 1.35-1.47 (m, 2H, CH$_2$), 1.64-1.85 (m, 4H, CH$_2$), 2.73-2.85 (m, 2H, CH$_2$), 3.03-3.06 (m, 1H, CH$_2$), 3.13-3.18 (m, 1H, CH$_2$), 3.32-3.37 (m, 1H, CH2), 3.52-3.62 (m, 1H, CH2), 3.73-3.81 (m, 1H, CH2), 4.10 (dd, 1H, CH), 6.30 (br s, 1H, NH), 7.08-7.20 (m, 4H, Ar-H), MS (ESI, +ve): m/z: 273 [M+H]$^+$.

Example 4

In this example, a method is provided for preparing intermediate (6) of R-praziquantel:

To a reactor, compound (11) (1.36 g, 5 mmol), compound (12) (0.67 g, 3.28 mmol) and tert-butyl methyl ether (30 mL) were added and stirred well before adding 12 mg of CAL-A (6000 u/g, L3420, Sigma) to start the reaction. The reaction was carried out under a temperature of 0° C. with stirring, monitored by HPLC and stopped after reacting for 66-68 hours. The resulting mixture was filtered to remove enzymes, washed with 10 mL of toluene, and the organic layer was concentrated under reduced pressure. The residues were separated through silica gel column chromatography (ethyl acetate/n-hexane=1:15) to obtain 0.52 g of intermediate (6). Yield: 38%, melting point: 112-114° C., ee value: >93%.

NMR data of intermediate (6): same as Example 3.

Example 5

In this example, a method is provided for preparing intermediate (6) of R-praziquantel.

To a reactor, compound (11) (1.36 g, 5 mmol), compound (12) (0.67 g, 3.28 mmol) and ethyl ether (30 mL) were added and stirred well before adding 20 mg of CAL-A (6000 u/g, L3420, Sigma) to start the reaction. The reaction was carried out under a temperature of 5° C. with stirring, monitored by HPLC and stopped after reacting for 46-48 hours. The resulting mixture was filtered to remove enzymes, washed with 10 mL of toluene, and the organic layer was concentrated under reduced pressure. The residues were separated through silica gel column chromatography (ethyl acetate/n-hexane=1:15) to obtain 0.61 g of intermediate (5). Yield: 45%, melting point: 111-112° C., ee value: >96%.

NMR data of intermediate (6): same as Example 3.

Example 6

In this example, a method is provided for preparing intermediate (6) of R-praziquantel.

To a reactor, compound (11) (1.36 g, 5 mmol), compound (12) (0.67 g, 3.28 mmol) and isopropyl ether (30 mL) were added and stirred well before adding 3 mg of CAL-B (5000 u/g, L3170, Sigma) to start the reaction. The reaction was carried out under a temperature of 30° C. with stirring, monitored by HPLC and stopped after reacting for 50-52 hours. The resulting mixture was filtered to remove enzymes, washed with 10 mL of toluene, and the organic layer was concentrated under reduced pressure. The residues were separated through silica gel column chromatography (ethyl acetate/n-hexane=1:15) to obtain 0.61 g of intermediate (6). Yield: 45%, melting point: 111- 112° C., ee value: >98%.

NMR data of intermediate (6): same as s Example 3.

Example 7

In this example, a method is provided for preparing intermediate (6) of R-praziquantel.

To a reactor, compound (11) (1.36 g, 5 mmol), compound (12) (0.67 g, 3.28 mmol) and tetrahydrofuran (30 mL) were added and stirred well before adding 20 mg of CAL-B (5000 u/g, L3170, Sigma) to start the reaction. The reaction was carried out under a temperature of 0° C. with stirring, monitored by HPLC and stopped after reacting for 41-42 hours. The resulting mixture was filtered to remove enzymes, washed with 10 mL of toluene, and the organic layer was concentrated under reduced pressure. The residues were separated through silica gel column chromatography (ethyl acetate/n-hexane=1:15) to obtain 0.58 g of intermediate (6). Yield: 43%, melting point: 114- 117° C., cc value: >56%.

NMR data of intermediate (6): same as Example 3.

Example 8

In this example, a method is provided for preparing intermediate (6) of R-praziquantel.

To a reactor, compound (11) (1.36 g, 5 mmol), compound (12) (0.67 g, 3.28 mmol) and dichloromethane (30 mL) were added and stiffed well before adding 12 mg of CAL-B (5000 u/g, L3470, Sigma) to start the reaction. The reaction was carried out under a temperature of 10° C. with stirring, monitored by HPLC and stopped after reacting for 60-62 hours. The resulting mixture was filtered to remove enzymes, washed with 10 mL of toluene, and the organic layer was concentrated under reduced pressure. The residues were separated through silica gel column chromatography (ethyl acetate/n-hexane=1:15) to obtain 0.6 g of intermediate (6). Yield: 44%, melting point: 112- 117° C., ee value: >58%.

NMR data of intermediate (6): same as Example 3.

Example 9

In this example, a method is provided for preparing intermediate (6) of R-praziquantel.

To a reactor, compound (11) (1.36 g, 5 mmol), compound (12) (0.67 g, 3.28 mmol) and n-hexane (30 mL) were added and stirred well before adding 2 mg of Novozyme 435 (10000 u/g, L4777, Sigma) to start the reaction. The reaction was carried out under a temperature of 50° C. with stirring, monitored by HPLC and stopped after reacting for 50-52 hours. The resulting mixture was filtered to remove enzymes, washed with 10 mL of toluene, and the organic layer was concentrated under reduced pressure. The residues were separated through silica gel column chromatography (ethyl acetate/n-hexane=1:15) to obtain 0.53 g of intermediate (6). Yield: 39%, melting point: 112- 114° C., ee value: >94%.

NMR data of intermediate (6): same as s Example 3.

Example 10

In this example, a method is provided for preparing intermediate (6) of R-praziquantel:

To a reactor, compound (11) (1.36 g, 5 mmol), compound (12) (0.67 g, 3.28 mmol) and acetonitrile (30 mL) were added and stirred well before adding 20 mg of Novozyme 435 (10000 u/g, L4777, Sigma) to start the reaction. The reaction was carried out under a temperature of 0° C. with stirring, monitored by HPLC and stopped after reacting for 50-52 hours. The resulting mixture was filtered to remove enzymes, washed with 10 mL of toluene, and the organic layer was concentrated under reduced pressure. The residues were separated through silica gel column chromatography (ethyl acetate/n-hexane=1:15) to obtain 0.58 g of intermediate (6). Yield: 43%, melting point: 112- 115° C., ee value: >83%, NMR data of intermediate (6): same as Example 3.

Example 11

In this example, a method is provided for preparing intermediate (6) of R-praziquantel:

To a reactor, compound (11) (1.36 g, 5 mmol), compound (12) (0.67 g, 3.28 mmol) and toluene (30 mL) were added and stirred well before adding 20 mg of Novozyme 435 (10000 u/g, L4777, Sigma) to start the reaction. The reaction was carried out under a temperature of 70° C. with stirring, monitored by HPLC and stopped after reacting for 6-7 hours. The resulting mixture was filtered to remove enzymes, washed with 10 mL of toluene, and the organic layer was concentrated under reduced pressure. The residues were separated through silica gel column chromatography (ethyl acetate/n-hexane=1:15) to obtain 0.58 g of intermediate (6). Yield: 43%, melting point: 111- 113° C., ee value: >97%.

NMR data of intermediate (6): same as Example 3.

Example 12

In this example, a method is provided for preparing R-praziquantel.

To a reactor, intermediate (6) (2.7 g, 10 mmol), ethyl acetate (30 mL) and anhydrous potassium carbonate (3.2 g, 23 mmol) were added and stirred well before adding chloroacetyl chloride (1.4 g, 12 mmol) dropwise to the reaction mixture. After the addition, the reaction was stirred under room temperature for 3 hours, till HPLC indicated the reaction was completed, and benzyltriethylammonium chloride (22.7 mg, 0.1 mmol) was added to the reaction mixture, and the reaction mixture was heated to reflux for 6-8 hours, till HPLC indicated the reaction was completed. The resulting mixture was filtered to remove insoluble substances and the ethyl acetate layer was washed with water and saturated saline solution successively, dried with anhydrous magnesium sulfate before removing solvents under reduced pressure to give a crude product. The crude product was recrystallized with absolute ethanol to obtain a pure product of R-praziquantel (7) (0.24 g). Yield: 78%, melting point: 113- 115° C., ee value: >99%.

NMR data of R-praziquantel; $^1$H NMR (400 MHz, CDCl$_3$): δ 1.21-1.96 (m, 10H, 5xCH$_2$), 2.45-2.50 (m, 1H, CH), 2.78-3.05 (m, 4H, CH$_2$), 4.10 (d, 1H, CH$_2$), 4.48 (d, 1H, CH$_2$), 4.79-4.85 (m, 2H, CH$_2$), 5.20 (d, 1H, CH), 7.12-7.30 (m, 4H, Ar-H). MS (ESI, +ve): m/z: 313 [M+H]$^+$.

Example 13

In this example, a method is provided for preparing R-praziquantel:

To a reactor, intermediate (6) (27 g), ethyl acetate (30 mL) and anhydrous potassium carbonate (32 g) were added and stirred well before adding chloroacetyl chloride (14 g) dropwise to the reaction mixture. After the addition, the reaction was stirred under room temperature for 4 hours, till HPLC indicated the reaction was completed, and benzyltriethylammonium chloride (0.23 g, 1 mmol) was added to the reaction mixture, and then the reaction mixture was heated to reflux for 9- 10 hours, till HPLC indicated the reaction was completed. The resulting mixture was filtered to remove insoluble substances and the ethyl acetate layer was washed with water and saturated saline solution successively, dried with anhydrous magnesium sulfate before removing solvents under reduced pressure to give a crude product. The crude product was recrystallized with absolute ethanol to obtain a pure product of R-praziquantel (7) (24 g). Yield: 78%, melting point: 113- 115° C., ee value: >99%.

NMR data of R-praziquantel: same as Example 12.

Example 14

Preparation of compound (8)

To a reactor, compound (1) (12.9 g, 0.1 mol), pyridine (0.4 g, 5 mmol) and sodium cyanide (5.9 g, 0.12 mol) were added prior to addition of 300 mL of water, 300 mL of 1,2-dichloroethane. The mixture was stirred well and cooled to −20° C., and cyclohexaformyl chloride (16.2 g, 0.11 mol) was added dropwise slowly with the temperature of the reaction mixture remained at −15° C. during the addition. After that, the reaction was stirred for another 4 hours under 0° C., then slowly heated to room temperature, till TLC indicated the raw materials were completely transformed, and diluted by adding 300 mL of dichloromethane. The organic phase was separated, dried with anhydrous sodium sulfate, filtered to remove the desiccant, and concentrated under reduced pressure to give 4 g of compound (8) as light yellow solid. Yield: 90%, melting point: 125- 127° C. Compound (8) can be used directly for further reaction without purification.

NMR data of compound (8): $^1$H NMR (400 MHz, CDCl$_3$): δ 1.32-1.86 (m, 10H, 5xCH$_2$), 2.35 (dd, 1H, CH), 6.08 (d, 1H, CH), 6.58 (s, 1H, CH), 6.65 (s, 1H, CH), 7.12-7.31 (m, 4H, Ar-H). MS (ESI, +ve): m/z: 267 [M+H]$^+$.

Example 15

Preparation of compound (11)

In a sealed container, compound (8) (3 g, 0.01 mol), absolute methanol (60 mL) and 10% catalyst Pd/C (0.2 g) were added. The air within the container was replaced with hydrogen before continuously feeding hydrogen (3 MPa), followed by heating to 65° C. The reaction was stirred for 4 hours till the reaction was indicated as completed. The catalyst was filtered and recovered and the reaction liquid was concentrated under reduced pressure. The residues were separated and purified through flash chromatography to obtain 2.6 g of compound (11) as solid. Yield: 95%. Melting point: 112-114° C.

NMR data of compound (11): $^1$H NMR (400 MHz, CDCl$_3$): δ 1.17-1.36 (m, 5H, CH$_2$), 1.65-1.76 (m, 5H, CH$_2$), 2.00-2.08 (m, 1H, CH), 2.85-3.01 (m, 2H, CH$_2$), 3.16-3.22 (m, 1H, CH2), 3.36-3.43 (m, 1H, CH$_2$), 3.52-3.62 (m, 1H, CH$_2$), 3.78-3.83 (m, 1H, CH$_2$), 4.48 (d, 1H, CH), 6.43(br s, 2H, NH), 7.07-7.20 (m, 4H Ar-H). MS (ESI, +ve): m/z: 273 [M+H]$^+$.

Example 16

In this example, a method is provided for preparing intermediate (15) of R-praziquantel.

*Aspergillas* protease (0.1 g of enzyme solution) (P6110, Sigma, 500 u/g) was added to potassium phosphate buffer solution (43 mL, pH 7.0, 0.1 M). N-((2-oxalylmonoethoxycarbonylacyl)-1,2,3,4-tetrahydroisoquinidine-1-yl)methyl) cyclohexanecar boxamide compound (13) (3.72 g, 10 mmol) was dissolved in 5 mL of acetonitrile, and then the acetonitrile solution was added into potassium phosphate buffer solution. The mixed solution was allowed to react under a temperature of 23° C. with vigorously stirring, and the pH of the reaction solution was controlled at 7.0 by adding 1 N sodium hydroxide solution continuously. The reaction was monitored by HPLC. When the conversion reached 50%, the reaction was quenched with dichloromethane and the product was extracted with the same. The organic layer of dichloromethane was concentrated under reduced pressure and the residues were separated through silica gel column chromatography (ethyl acetate/n-hexane=1:20) to obtain 1.3 g of intermediate (15). Yield: ~38%, ee value: 99%.

NMR data of intermediate (15): $^1$H NMR (400 MHz, CDCl$_3$): δ 1.32-1.86 (m, 10H, 5xCH2), 2.73-2.85 (m, 2H, CH$_2$), 3.05-3.06 (m, 1H, CH$_2$), 3.11-3.18 (m, 1H, CH$_2$), 3.32-3.37 (m, 1H, CH$_2$), 3.53-3.62 (m, 1H, CH$_2$), 3.73-3.81(m, 1H, CH$_2$), 5.12 (dd, 1H, CH), 7.17-7.20 (m, 4H, Ar-H).

Example 17

In this example, a method is provided for preparing intermediate (15) of R-praziquantel.

*Aspergillus* protease (0.2 g of enzyme solution) (P6110, Sigma, 500 u/g) was added to potassium phosphate buffer solution (43 mL, pH 7.0, 0.1 M). N-((2-oxalylmonoethoxycarbonylacyl)-1,2,3,4-tetrahydroisoquinidine-1-yl)methyl)cyclohexanecar boxamide compound (13) (3.72 g) was dissolved in 5 mL of toluene, and then the toluene solution was added into potassium phosphate buffer solution. The mixed solution was allowed to react under a temperature of 0° C. with vigorously stirring, and the pH of the reaction solution was controlled at 7.0 by adding 1 N sodium hydroxide solution continuously. The reaction was monitored by HPLC. When the conversion reached 40%, the reaction was quenched with dichloromethane and the product was extracted with the same. The organic layer of dichloromethane was concentrated under reduced pressure, and the residues were separated through silica gel column chromatography (ethyl acetate/n-hexane=1:20) to obtain 1.1 g of intermediate (15). Yield: ~31%, ee value: 89%.

NMR data of intermediate (15): same as Example 16.

Example 18

In this example, a method is provided for preparing intermediate (15) of R-praziquantel;

*Aspergillus* protease (0.2 g of enzyme solution) (P6110, Sigma, 500 u/g) was added to potassium phosphate buffer solution (43 mL, pH 7.0, 0.1 M). N-((2-oxalylmonoethoxycarbonylacyl)-1,2,3,4-tetrahydroisoquinidine-1-yl)methyl) cyclohexanecar boxamide compound (13) (3.72 g) was dissolved in 5 mL of DMSO, and then the DMSO solution was added into potassium phosphate buffer solution. The mixed solution was allowed to react under a temperature of 70° C. with vigorously stirring, and the pH of the reaction solution was controlled at 7.0 by adding 1 N sodium hydroxide solution continuously. The reaction was monitored by HPLC. When the conversion reached 60%, the reaction was quenched with dichloromethane and the product was extracted with the same. The organic layer of dichloromethane was concentrated under reduced pressure and the residues were separated through silica gel column chromatography (ethyl acetate/n-hexane=1:20) to obtain 1.3 g of intermediate (15). Yield: ~38%. ee value: 99%.

NMR data of intermediate (15): same as Example 16.

Example 19

In this example, a method is provided for preparing intermediate (15) of R-praziquantel:

Papain (50 mg of enzyme powder) (AD244857, 23 u/mg, Guangzhou Howei Chemical Co., LTD) was added to potassium phosphate buffer solution (43 mL, pH 6.8, 0.1 M). N-((2-oxalymonoethoxycarbonylacyl)-1,2,3,4-tetrahydroisoquinidine-1-yl)cyclohexanecarboxamide compound (13) (3.72 g) was dissolved in 5 mL of acetonitrile, and then the acetonitrile solution was added into potassium phosphate buffer solution. The mixed solution was allowed to react under a temperature of 30° C. with vigorously stirring, and the pH of the reaction solution was controlled at 7.0 by adding 1N sodium hydroxide solution continuously. The reaction was monitored by HPLC. When the conversion reached 50%, the reaction was quenched with dichloromethane and the product was extracted with the same. The organic layer of dichloromethane was concentrated under reduced pressure and the residues were separated through silica gel column chromatography (ethyl acetate/n-hexane=1:20) to obtain 1.2 g of intermediate (15). Yield: ~35%, ee value: 99%.

NMR data of intermediate (15): same as Example 16.

Example 20

In this example, a method is provided for preparing intermediate (15) of R-praziquantel:

Papain (50 mg 0.1 g of enzyme powder) (AD244857, 23 u/mg, Guangzhou Howei Chemical Co., LTD) was added to potassium phosphate buffer solution (43 mL, pH 7.0, 0.1 M). N-((2-oxalylmonoethoxycarbonylacyl)-1,2,3,4-tetrahydroisoquinidine-1-yl)methyl)cyclohexanecarboxamide compound (13) (3.72 g) was dissolved in 5 mL of DMF, and then the DMF solution was added into potassium phosphate buffer solution. The mixed solution was allowed to react under a temperature of 0° C. with vigorously stirring, and the pH of the reaction solution was controlled at 7.0 by adding 1 N sodium hydroxide solution continuously. The reaction was monitored by HPLC. When the conversion reached 40%, the reaction was quenched with dichloromethane and the product was extracted with the same. The organic layer of dichloromethane was concentrated under reduced pressure and the residues were separated through silica gel column chromatography (ethyl acetate/n-hexane=1:20) to obtain 1.1 g of intermediate (15). Yield: ~31%, ee value: 88%.

NMR data of intermediate (15): same as Example 16.

Example 21

In this example, a method is provided for preparing intermediate (5) of R-praziquantel:

Papain (50 mg 0.1 g of enzyme powder) (AD244857, 23 u/mg, Guangzhou Howei Chemical Co., LTD) was added to potassium phosphate buffer solution (43 mL, pH 7.0, 0.1 M). N-((2-oxalylmonoethoxycarbonylacyl)-1,2,3,4-tetrahydroisoquinidine-1-yl)methyl)cyclohexanecarboxamide compound (13) (3.72 g) was dissolved in 5 mL of 1,4-dioxane, and then the 1,4-dioxane solution was added into potassium phosphate buffer solution. The mixed solution was allowed to react under a temperature of 70° C. with vigorously stirring, and the pH of the reaction solution was controlled at 7.0 by adding 1 N sodium hydroxide solution continuously. The reaction was monitored by HPLC. When the conversion reached 60%, the reaction was quenched with dichloromethane and the product was extracted with the same. The organic layer of dichloromethane was concentrated under reduced pressure and the residues were separated through silica gel column chromatography (ethyl acetate/n-hexane=1: 20) to obtain 1.23 g of intermediate (15). Yield: ~36%, ee value: 99%.

NMR data of intermediate (15): same as Example 16.

Example 22

In this example, a method is provided for preparing intermediate (15) of R-praziquantel:

*Bacillus* protease (0.5 g of enzyme solution) (SG170459, 2.4 u/g, Sigma Guangzhou Howei Chemical Co., LTD) was added to potassium phosphate buffer solution (43 mL, pH 7.0, 0.1 M).

N-((2-oxalylmonoethoxycarbonylacyl)-1,2,3,4-tetrahydroisoquinidine-1-yl)methyl)cyclohexanecarboxamide compound (13) (3.72 g) was dissolved in 5 mL of DMSO, and then the DMSO solution was added into potassium phosphate buffer solution. The mixed solution was allowed to react under a temperature of 30° C. with vigorously stirring, and the pH of the reaction solution was controlled at 7.0 by adding 1 N sodium hydroxide solution continuously. The reaction was monitored by HPLC. When the conversion reached 50%, the reaction was quenched with dichloromethane and the product was extracted with the same. The organic layer of dichloromethane was concentrated under reduced pressure and the residues were separated through silica gel column chromatogaphy (ethyl acetate/n-hexane=1:20) to obtain 1.1 g of intermediate (15). Yield: ~32%, ee value: 99%.

NMR data of intermediate (15): same as Example 16.

Example 23

In this example, a method is provided for preparing intermediate (15) of R-praziquantel:

*Bacillus* protease (0.5 g of enzyme solution) (SG170459, 2.4 u/g, Guangzhou Howei. Chemical Co., LTD) was added to potassium phosphate buffer solution (43 mL, pH 7.0, 0.1 M). N-((2-oxalylmonoethoxycarbonylacyl)-1,2,3,4-tetrahydroisoquinidine-1-yl)methyl)cyclohexanecarboxamide compound (13) (3.72 g) was dissolved in 5 mL of 1,4-dioxane, and then the 1,4-dioxane solution was added into potassium phosphate buffer solution. The mixed solution was allowed to react under a temperature of 0° C. with vigorously stirring, and the pH of the reaction solution was controlled at 7.0 by adding 1 N sodium hydroxide solution continuously. The reaction was monitored by HPLC. When the conversion reached 40%, the reaction was quenched with dichloromethane and the product was extracted with the same. The organic layer of dichloromethane was concentrated under reduced pressure and the residues were separated through silica gel column chromatogaphy (ethyl acetate/n-hexane=1: 20) to obtain 1 g of intermediate (15). Yield: ~30%, ee value; 86%.

NMR data of intermediate (15): same as Example 16.

Example 24

In this example, a method is provided for preparing intermediate (15) of R-praziquantel:

*Bacillus* protease (0.5 g of enzyme solution) (SG170459, 2.4 u/g, Guangzhou Howei Chemical Co., LTD) was added to potassium phosphate buffer solution (43 mL, pH 7.0, 0.1 M). N-((2-oxalylmonoethoxycarbonylacyl)-1,2,3,4-tetrahydroisoquinidine-1-yl)methyl)yclohexanecar boxamide compound (13) (3.72 g was dissolved in 5 mL of 1,4-dioxane, and then the 1,4-dioxane solution was added into potassium phosphate buffer solution. The mixed solution was allowed to react under a temperature of 70° C. with vigorously stirring, and the pH of the reaction solution was controlled at 7.0 by adding 1 N sodium hydroxide solution continuously. The reaction was monitored by HPLC. When the conversion reached 60%, the reaction was quenched with dichloromethane and the product was extracted with the same. The organic layer of dichloromethane was concentrated under reduced pressure and the residues were separated through silica gel column chromatography (ethyl acetate/n-hexane=1:20) to obtain 1.1 g of intermediate (15). Yield: ~31%, ee value: 99%.

NMR data of intermediate (15): same as Example 16.

Example 25

In this example, a method is provided for preparing intermediate (15) of R-praziquantel:

Bacillus licheniformis protease (0.3 g of enzyme solution) (P5985, 16 u/g, Sigma) was added to potassium phosphate buffer solution (43 mL, pH 7.2, 0.1 M). N-((2-oxalylmonoethoxycarbonylacyl)-1,2,3,4-tetrahydroisoquinidine-1-yl)methyl)cyclohexanecarboxamide compound (13) (3.72 g) was dissolved in 5 mL of methanol, and then the methanol solution was added into potassium phosphate buffer solution. The mixed solution was allowed to react under a temperature of 30° C. with vigorously stirring, and the pH of the reaction solution was controlled at 7.2 by adding 1 N sodium hydroxide solution continuously. The reaction was monitored by HPLC. When the conversion reached 50%, the reaction was quenched with dichloromethane and the product was extracted with the same. The organic layer of dichloromethane was concentrated under reduced pressure and the residues were separated through silica gel column chromatography (ethyl acetate/n-hexane=1:20) to obtain 0.96 g of intermediate (15). Yield: ~28%, ee value: 99%.

NMR data of intermediate (15): same as Example 16.

Example 26

In this example, a method is provided for preparing intermediate (15) of R-praziquantel:

Bacillus licheniformis protease (0.3 g of enzyme solution) (P5985, 16 u/g, Sigma) was added to potassium phosphate buffer solution (43 mL, pH 7.0, 0.1 M). N-((2-oxalylmonoethoxycarbonylacyl)-1,2,3,4-tetrahydroisoquinidine-1-yl)methyl)cyclohexanecarboxamide compound (13) (3.72 g) was dissolved in 5 mL of methanol, and the methanol solution was added into potassium phosphate buffer solution. The mixed solution was allowed to react under a temperature of 0° C. with vigorously stirring, and the pH of the reaction solution was controlled at 7.2 by adding 1 N sodium hydroxide solution continuously. The reaction was monitored by HPLC. When the conversion reached 40%, the reaction was quenched with dichloromethane and the product was extracted with the same. The organic layer of dichloromethane was concentrated under reduced pressure and the residues were separated through silica gel column chromatography (ethyl acetate/n-hexane=1:20) to obtain 1.1 g of intermediate (15). Yield: ~31%, ee value: 89%, NMR data of intermediate (15): same as Example 16.

Example 27

In this example, a method is provided for preparing intermediate (15) of R-praziquantel:

Bacillus licheniformis protease (0.5 g of enzyme solution) (P5985, 16 u/g, Sigma) was added to potassium phosphate buffer solution (43 mL, pH 7.2, 0.1 M). N-((2-oxalylmonoethoxycarbonylacyl)-1,2,3,4-tetrahydroisoquinidine-1-yl)methyl)cyclohexane-carboxamide compound (13) (3.72 g) was dissolved in 5 mL acetonitrile, and the acetonitrile solution was added into potassium phosphate buffer solution. The mixed solution was allowed to react under a temperature of 70° C. with vigorously stirring, and the pH of the reaction solution was controlled at 7.2 by adding 1 N sodium hydroxide solution continuously. The reaction was monitored by HPLC. When the conversion reached 60%, the reaction was quenched with dichloromethane and the product was extracted with the same. The organic layer of dichloromethane was concentrated under reduced pressure and the residues were separated through silica gel column chromatography (ethyl acetate/n-hexane=1:20) to obtain 1.2 g of intermediate (15). Yield: ~35%, ee value: 99%.

NMR data of intermediate (15): same as Example 16.

Example 28

In this example, a method is provided for preparing intermediate (15) of R-praziquantel:

Chymotrypsin (5 mg of enzyme powder) (C4129, ≥40 u/mg, Sigma) was added to potassium phosphate buffer solution (43 mL, pH 7.0, 0,1 M). N-((2-oxalylmonoethoxycarbonylacyl)-1,2,3,4-tetrahydroisoquinidine-1-yl)methyl)cyclohexanecarboxamide compound (13) (3.72 g) was dissolved in 5 mL of ethanol, and the ethanol solution was added into potassium phosphate buffer solution. The mixed solution was allowed to react under a temperature of 30° C. with vigorously stirring, and the pH of the reaction solution was controlled at 7.0 by adding 1 N sodium hydroxide solution continuously. The reaction was monitored by HPLC. When the conversion reached 50%, the reaction was quenched with dichloromethane and the product was extracted with the same. The organic layer of dichloromethane was concentrated under reduced pressure and the residues were separated through silica gel column chromatography (ethyl acetate/n-hexane=1:20) to obtain 1.24 g of intermediate (15). Yield: ~36%, ee value: 99%.

NMR data of intermediate (15): same as Example 16.

Example 29

In this example, a method is provided for preparing intermediate (15) of R-praziquantel:

Chymotrypsin (5 mg of enzyme powder) (C4129, ≥40 u/mg, Sigma) was added to potassium phosphate buffer solution (43 mL, pH 7.0, 0.1 M). N-((2-oxalylmonoethoxycarbonylacyl)-1,2,3,4-tetrahydroisoquinidine-1-yl)methyl)cyclohexanecarboxamide compound (13) (3.72 g) was dissolved in 5 mL of ethanol, and the ethanol solution was added into potassium phosphate buffer solution. The mixed solution was allowed to react under a temperature of 0° C. with vigorously stirring, and the pH of the reaction solution was controlled at 7.0 by adding 1 N sodium hydroxide solution continuously. The reaction was monitored by HPLC. When the conversion reached 40%, the reaction was quenched with dichloromethane and the product was extracted with the same. The organic layer of dichloromethane was concentrated under reduced pressure and the residues were separated through silica gel column chromatography (ethyl acetate/n-hexane=1:20) to obtain 1.1 g of intermediate (15). Yield: ~31%, ee value: 93%.

NMR data of intermediate (15): same as Example 16.

Example 30

In this example, a method is provided for preparing intermediate (15) of R-praziquantel:

Chymotrypsin (10 mg of enzyme powder) (C4129, ≥40 u/mg, Sigma) was added to potassium phosphate buffer solution (43 mL, pH 7.0, 0.1 M). N-((2-oxalylmonoethoxycarbonylacyl)-1,2,3,4-tetrahydroisoquinidine-1-yl)methyl)cyclohexanecarboxamide compound (13) (3.72 g) was dissolved in 5 mL of DMSO, and the DMSO solution was added into potassium phosphate buffer solution. The mixed solution was allowed to react under a temperature of 70° C. with vigorously stirring, and the pH of the reaction solution was controlled at 7.0 by adding 1 N sodium hydroxide solution continuously. The reaction was monitored by HPLC. When the conversion reached 40%, the reaction was quenched with dichloromethane and the product was extracted with the same. The organic layer of dichloromethane was concentrated under reduced pressure and the residues were separated through silica gel column chromatography (ethyl acetate/n-hexane=1:20) to obtain 1.14 g of intermediate (15). Yield: ~33%, ee value: 87%.

NMR data of intermediate (15): same as Example 16.

Example 31

Preparation of compound (6):
Intermediate (15) (3.44 g, 10 mmol) was added into 4 N HCl (20 mL) within a reactor, heated to reflux for 5-6 hours, and the reaction was monitored by HPLC. When the raw materials were transformed completely, the reaction was stopped and the reaction mixture was extracted with dichloromethane. The pH of the water layer was regulated to 10-11, and said layer was then extracted with dichloromethane (2×20 mL), dried with anhydrous sodium sulfate, filtered to remove the desiccant, and distilled to remove the solvent dichloromethane, to obtain 2.58 g of optically pure N-((1,2,3,4-tetrahydroisoquinidine-1-yl)cyclohexanecarboxamide compound 6. Yield: 95%, melting point: 111-112° C., ee value: 99%. Compound (6) can be used for the next reaction without further purification.
NMR data of compound (6): $^1$H NMR (400 MHz, CDCl$_3$): δ 1.16-1.27 (m, 4H, CH$_2$), 1.35-1.47(m, 2H, CH$_2$), 1.64-1.85 (m, 4H, CH$_2$), 2.73-2.85 (m, 2H, CH$_2$), 3.03-3.06 (m, 1H, CH$_2$), 3.13-3.18 (m, 1H, CH$_2$), 3.32-3.37 (m, 1H, CH$_2$), 3.52-3.62(m, 1H, CH$_2$), 3.73-3.81(m, 1H, CH2), 4.10 (dd, 1H, CH), 6.30 (br s, 1H, NH), 7.08-7.20 (m, 4H, Ar-H), MS (ESI, +ve): m/z: 273 [M+H]$^+$.

Example 32

In this example, a method is provided for preparing R-praziquantel:
Compound. (6) (2.7 g, 10 mmol), ethyl acetate (30 mL) and anhydrous potassium carbonate (3.2 g, 23 mmol) were added into a reactor and well stirred. Chloroacetyl chloride (1.4 g, 12 mmol) was added dropwise into the reaction mixture before stirring under room temperature for 3 hours, till HPLC indicated the, reaction was completed. To the reaction mixture, benzyltriethylammonium chloride (22.7 mg, 0.1 mmol) was added, and then the reaction mixture was heated to reflux for 6-8 hours till HPLC indicated the reaction was completed. Filtration was carried out to remove insoluble substances, and the layer of ethyl acetate was washed with water and saturated saline solution successively, dried with anhydrous magnesium sulfate, prior to removing solvent under reduced pressure to give a crude product. The crude product was recrystallized with absolute ethanol to obtain a pure product R-praziquantel (7) (0,24 g). 78%, melting point: 113-115° C., ee value: >99%.
NMR data of R-praziquantel: $^1$H NMR (400 MHz, CDCl$_3$): δ 1.21-1.96 (m, 10H, 5xCH$_2$), 2.45-2.50 (m, 1H, CH), 2.78-3.05 (m, 4H, CH$_2$), 4.10 (d, 1H, CH$_2$), 4.48 (d, 1H, CH$_2$), 4.79-4.85 (m, 2H, CH$_2$), 5.20 (d, 1H, CH), 7.12-7.30 (m, 4H, Ar-H). MS (ESI, +ve): m/z: 313 [M+H]$^+$.

Example 33

Preparation of compound (8)
To a reactor, compound (1) (12.9 g, 0.1 mol), pyridine (0.4 g, 5 mmol) and sodium cyanide (5.9 g, 0.12 mol) were added, then adding 300 mL of water, 300 mL of 1,2-dichloroethane. The mixture was stirred well and cooled to –20° C., to which cyclohexaformyl chloride (16.2 g, 0.11 mol) was added dropwise slowly and the temperature of the reaction mixture was remained at –15° C. during the addition. After that, the reaction was stirred for another 4 hours under 0° C. and slowly heated to room temperature. When TCL indicated the raw materials were transformed completely, the reaction was diluted by adding 300 mL of dichloromethane. The organic layer was separated, dried with anhydrous sodium sulfate, filtered to remove the desiccant and concentrated under reduced pressure to obtain 4 g of compound (8) as light yellow solid. Yield: 90%, melting point: 125-127° C. Compound (8) can be used directly for the next reaction without further purification.
NMR data of compound (8): $^1$H NMR (400 MHz, CDCl$_3$): δ 1.32-1.86 (m, 10H, 5xCH$_2$), 2.35 (dd, 1H, CH), 6.08 (d, 1H, CH), 6.58 (s, 1H, CH), 6.65 (s, 1H, C 7.12-7.31 (m, 4H, Ar-H). MS (ESI, +ve): m/z: 267 [M+H]$^+$.

Example 34

Preparation of compound (11)
In a sealed container, compound (8) (3 g, 0.01 mol), 60 mL of absolute methanol and 10% catalyst Pd/C (0.2 g) were added. The air in the container was replaced with hydrogen before continuously feeding hydrogen (3 MPa) and then the reaction was heated to 65° C. and stirred for 4 hours. When the reaction was indicated as completed, the catalyst was recovered and the reaction liquid was concentrated under reduced pressure, The residues were separated and purified through flash chromatography to obtain 2.6 g of compound (11) as solid. Yield: ~95%. Melting point: 112- 114° C.
NMR data of compound (11): $^1$H NMR (400 MHz, CDCl$_3$): δ 1.17-1.36 (m, 5H, CH$_2$), 1.65-1.76 (m, 5H, CH$_2$), 2.00-2.08 (m, 1H, CH), 2.85-3.01 (m, 2H, CH$_2$), 3.16-3.22 (m, 1H, CH$_2$), 3.36-3.43 (m, 1H, CH$_2$), 3.52-3.62 (m, 1H, CH$_2$), 3.78-3.83 (m, 1H, CH$_2$), 4.48 (d, 1H, CH), 6.43(br s, 2H, NH), 7.07-7.20 (m, 4H, Ar-H). MS (ESI, +ve): m/z: 273 [M+H]$^+$.

Example 35

Preparation of compound (13)
In a reactor, N-((1,2,3,4-tetrahydroisoquinoline-1-yl)cyclohexanecarboxamide compound (11) (2.7 g, 10 mmol), 30 mL of dichloromethane and sodium bicarbonate (2.1 g, 25 mmol) were added and cooled to 10° C. The mixed solution of ethyl oxalyl monochloride (1.5 g, 11 mmol) and 15 mL of dichloromethane was added dropwise with stirring, and the temperature of the reaction mixture was remained no higher than 15° C. during the addition. After that, the reaction was warmed naturally to room temperature and stirred for another 10 hours, and then filtered to remove insoluble substances. 30 mL of water was added into the solution and stirred for 30 minutes before standing for stratification, drying with anhydrous sodium sulfate, filtering to remove the desiccant and distilled to remove the solvent dichloromethane to give 3.47 g of crude product N-((2-oxalylmonoethoxycarbonylacyl-1,2,3,4-tetrahydroisoquinidine-1-yl)methyl)cyclohexanecarboxamide compound 13. Yield: ~92%. Compound (13) can be used directly for the next enzymatic catalysis without further purification.
NMR data of compound (13): $^1$H NMR (400 MHz, CDCl$_3$): d 1.28-1.31(t, 3H, CH$_3$), 1.32-1.86 (m, 10H, 5xCH$_2$), 2.73-2.85 (m, 2H, CH$_2$), 3.03-3.06 (m, 1H, CH$_2$), 3.13-3.18 (m, 1H, CH$_2$), 3.32-3.37 (m, 1H, CH$_2$), 3.52-3.62 (m, 1H, CH$_2$), 3.73-3.81 (m, 1H, CH$_2$), 4.19-4.24 (m, 2H, —CH$_2$CH$_3$), 5.10 (dd, 1H, CH), 7.17-7.20 (m, 4H, Ar-H).

Disclosed hereinabove are description of specific embodiments of the invention, and the scope of protection of the invention is not only limited to the above embodiments. Various modifications to the invention within the scope of the relevant art can be performed with common knowledge.

The invention claimed is:

1. A method for preparing an intermediate for the synthesis of R-praziquantel, of formula (4), comprising contacting compound (2) with a lipase in a reaction mixture at a temperature of 0-80°C. to obtain compound of formula (4);

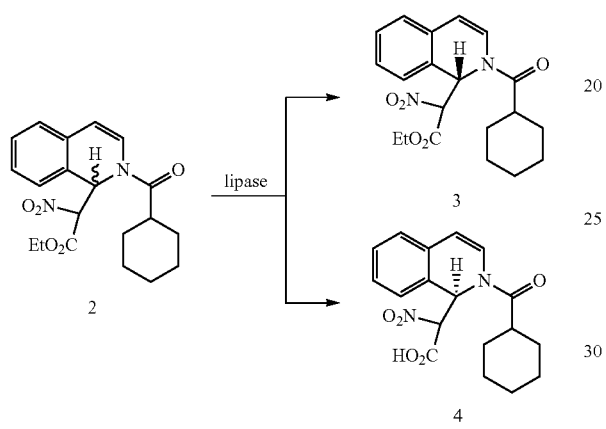

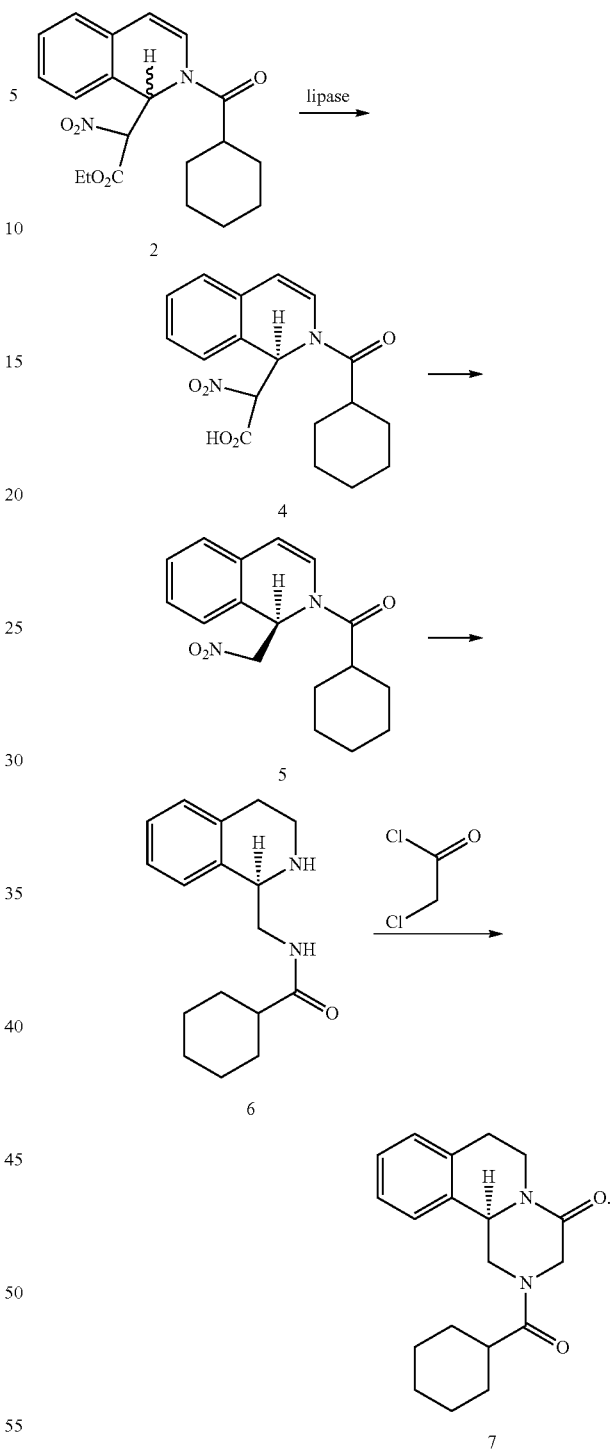

wherein the lipase comprises one or more lipases derived from *Aspergillus niger, Candida rugosa, Rhizomucor miehei, Candida antarctica, Pseudomonas cepacia, Pseudomonas fluorescens, Thermomyces lanuginose, Bacillus subtillis, Fusarium solani pisi, Alcaligenes spp., Rhizopus niveus, Mucor javanicus, Rhizopus oryzae,* and *Fusarium solani* (Mart.) sacc.

2. The method of claim 1, wherein the lipase is *Thermomyces lanuginosus* lipase, *Candida antarctica* lipase, *Candida rugosa* lipase, *Pseudomonas cepacia* lipase, or *Pseudomonas fluorescens* lipase.

3. The method of claim 1, wherein, the reaction mixture contains compound of formula (2) and the lipase in a ratio range of 100:0.5-100:3 (w/w).

4. The method of claim 1, wherein the reaction mixture contains phosphate buffer.

5. The method of claim 1, wherein the reaction mixture is incubated for 1-48 hours.

6. A method for preparing R-praziquantel, comprising the following steps:
  (a) preparing compound of formula (4) according to the method of any of claims 1-5;
  (b) decarboxylating the compound of formula (4) in an organic solvent to give compound of formula (5);
  (c) catalytic hydrogenation of the compound of formula (5) in an organic solvent to give compound of formula (6); and
  (d) contacting the compound of formula (6) with chloroacetyl chloride in an organic solvent to give compound of formula (7), R-praziquantel;

7. The method of claim 6, wherein the catalyst used in the catalytic hydrogenation in step (c) is selected from the group consisting of 5% Ru containing Ru/C catalyst, 10% Pd/C catalyst, and 10% Raney-Ni catalyst.

8. The method of claim 6, wherein the organic solvent in step (b) is selected from the group consisting of DMSO, N-methyl-2-pyrrolidone, acetonitrile, 1,4-dioxane, and combinations thereof.

9. The method of claim 6, wherein the organic solvent in step (c) is selected from the group consisting of absolute methanol, absolute ethanol, ethyl acetate, tetrahydrofuran, and combinations thereof.

10. The method of claim 6, wherein:
the organic solvent in step (d) is selected from the group consisting of dichloromethane, methyl tert-butyl ether, ethyl acetate, and combinations thereof.

* * * * *